(12) United States Patent
Govindappa et al.

(10) Patent No.: US 8,778,659 B2
(45) Date of Patent: Jul. 15, 2014

(54) METHOD OF REDUCING GLYCOSYLATION OF PROTEINS, PROCESSES AND PROTEINS THEREOF

(75) Inventors: Nagaraj Govindappa, Karnataka (IN); Komal Kanojia, Karnataka (IN); Krishnamurthy Venkatesan, Tamil Nadu (IN); Nitesh Dave, Karnataka (IN); Mukesh Babuappa Patale, Maharashtra (IN); Sanjay Tiwari, Karnataka (IN); Kedarnath N. Sastry, Karnataka (IN); Harish Iyer, Karnataka (IN)

(73) Assignee: Biocon Limited, Bangalore, Karnataka (IN)

( * ) Notice: Subject to any disclaimer, the term of this patent is extended or adjusted under 35 U.S.C. 154(b) by 0 days.

(21) Appl. No.: 13/578,403

(22) PCT Filed: Mar. 29, 2010

(86) PCT No.: PCT/IN2010/000190
§ 371 (c)(1),
(2), (4) Date: Aug. 10, 2012

(87) PCT Pub. No.: WO2011/099028
PCT Pub. Date: Aug. 18, 2011

(65) Prior Publication Data
US 2012/0309935 A1   Dec. 6, 2012

(30) Foreign Application Priority Data

Feb. 10, 2010 (IN) .............................. 332/CHE/2010

(51) Int. Cl.
*C12N 1/00* (2006.01)
*C12N 15/00* (2006.01)

(52) U.S. Cl.
USPC ............... 435/254.23; 435/243; 435/254.11; 435/320.1

(58) Field of Classification Search
None
See application file for complete search history.

(56) References Cited

U.S. PATENT DOCUMENTS

| 7,091,032 B2 * | 8/2006 | Annibali ................. 435/254.23 |
| 8,206,949 B2 * | 6/2012 | Bobrowicz et al. ........... 435/69.1 |
| 2011/0021378 A1 * | 1/2011 | Callewaert et al. ............ 506/16 |

OTHER PUBLICATIONS

Deckert 1980. Diabetes Care 3:623-626.*
Hartman 2008. Clin Med and Res. 6:54-67.*
Zinman 2013. Diabetes, Obesity and Metab. 15(Suppl.):6-10.*

* cited by examiner

*Primary Examiner* — Shulamith H Shafer
(74) *Attorney, Agent, or Firm* — Harness, Dickey & Pierce, PLC

(57) ABSTRACT

The disclosure relates to method of reducing O-glycosylation levels of the insulin or insulin analog precursor molecule produced by *Pichia* sp. The present disclosure provides genetically engineered knock-out strains of methylotrophic yeast including *Pichia* and especially *Pichia pastoris* by disruption of Protein mannosyl transferase (PMT) genes and rendering them capable of producing heterologous proteins with reduced glycosylation. Vectors, which comprise coding sequences for PMT1, PMT2, PMT4, PMT5, and PMT6 genes, for transforming methylotrophic yeasts are contemplated by the present disclosure. PMT inactivated strains of this disclosure have been deposited at MTCC, Chandigarh. The strains are PMT1/GS115 (MTCC 5515), PMT4/GS115 (MTCC 5516), PMT5/GS115 (MTCC 5517) and PMT6/GS115 (MTCC 5518).

18 Claims, 9 Drawing Sheets

SEQUENCE LISTING

```
<160> NUMBER OF SEQ ID NOS: 24

<210> SEQ ID NO 1
<211> LENGTH: 2313
<212> TYPE: DNA
<213> ORGANISM: Pichia pastoris
<220> FEATURE:
<221> NAME/KEY: gene
<222> LOCATION: (1)..(2313)

<400> SEQUENCE: 1
atgagtaaaa caagtcctca agaggtgcca gaaaacacta ctgagcttaa aatctcaaaa      60
ggagagctcc gtccttttat tgtgacctct ccatctcctc aattgagcaa gtctcgttct     120
gtgacttcaa ccaaggagaa gctgatattg gctagtttgt tcatatttgc aatggtcatc     180
aggttccaca acgtcgccca ccctgacagc gttgtgtttg atgaagttca ctttgggggg     240
tttgccagaa agtacatttt gggaaccttt ttcatggatt ttcatccgcc attggccaag     300
ctattatttg ctggtgttgg cagtcttggt ggatacgatg gagagtttga gttcaagaaa     360
attggtgacg aattcccaga gaatgttcct tatgtgctca tgagatatct tccctctggt     420
atgggagttg gaacatgtat tatgttgtat ttgactctga gagcttctgg ttgtcaacca     480
atagtctgtg ctctgacaac cgctcttttg atcattgaga atgctaatgt tacaatctcc     540
agattcattt tgctggattc gccaatgctg ttttttattg cttcaacagt ttactctttc     600
aagaaatttc aaattcagga accgtttacc ttccaatggt acaagaccct tattgctact     660
ggtgtttctt tagggttagc agcttccagt aaatgggttg gtttgttcac cgttgcctgg     720
attggattga taacaatttg ggacttatgg ttcatcattg gtgatttgac tgtttctgta     780
aagaaaattt tcggccattt tatcaccaga gctgtagctt tcttagtcgt ccccactctg     840
atctacctca ctttctttgc catccatttg caagtcttaa ccaaggaagg tgatggtggt     900
gctttcatgt cttccgtctt cagatcgacc ttagaaggta atgctgttcc aaaacagtcg     960
ctggccaacg ttggtttggg ctctttagtc actatccgtc atttgaacac cagaggtggt    1020
tacttacact ctcacaatca tctttacgag ggtggttctg gtcaacagca ggtcaccttg    1080
tacccacaca ttgattctaa taatcaatgg attgtacagg attacaacgc gactgaggag    1140
ccaactgaat ttgttccatt gaaagacggt gtccaaatca gattaaacca caaattgact    1200
tcccgaagat tgcactctca taacctcaga ccctcctgtg atgaacaaga ttggcaaaat    1260
gaggtatctg cttatggaca tgagggcttt ggcggtgatg ccaatgatga ctttgttgtg    1320
gagattgcca aggatctttc aactactgaa gaagctaagg aaaacgttag ggccattcaa    1380
```

```
actgttttta gattgagaca tgcgatgact ggttgttact tgttctccca cgaagtcaag    1440
cttcccaagt gggcatatga gcaacaagag gttacttgtg ctactcaagg tatcaaacca    1500
ctatcttact ggtacgttga gaccaacgaa aacccattct tggataaaga ggttgatgaa    1560
atagttagct atcctgttcc gactttcttt caaaaggttg ccgagctaca cgccagaatg    1620
tggaagatca acaagggctt aactgatcat catgtctatg aatccagtcc agattcttgg    1680
cccttcctgc tcagaggtat aagctactgg tcaaaaaatc actcacaaat ttatttcata    1740
ggtaatgctg tcacttggtg gacagtcacc gcaagtattg cttttgttctc tgtctttttg    1800 gttttctcta ttctgagatg gcaaagaggt tttgggttca gcgttgaccc aactgtgttc    1860
aacttcaatg ttcaaatgct tcattacatc ctaggatggg tactgcatta cttgccatct    1920
ttccttatgg cccgtcagct atttttgcac cactatctac catcattgta ctttggtata    1980
ttggctctcg acatgtgtt tgagattatt cactcttatg tcttcaaaaa caaacaggtt    2040
gtgtcttact ccatattcgt tctctttttt gccgttgcgc tttctttctt ccaaagatat    2100
tctccattga tctatgcagg acgatggacc aaggaccaat gcaacgaatc caagatactc    2160
aagtgggact ttgactgtaa caccttcccc agtcacacat ctcagtatga atatgggca    2220 tcccctgtac aaacttccac tcctaaagaa ggaacccact cagaatctac cgtcggagaa    2280
cctgacgttg agaagctggg agagacagtc taa                                2313
```

```
<210> SEQ ID NO 2
<211> LENGTH: 2316
<212> TYPE: DNA
<213> ORGANISM: Pichia pastoris
<220> FEATURE:
<221> NAME/KEY: gene
<222> LOCATION: (1)..(2316)

<400> SEQUENCE: 2
```

```
atgggtggtg gattaattcc tttcgattct tattttttat cttcgatgac aggccgtgtc      60
gaccagaaat ctgatcagaa ggtgaaggaa ttgatcgaaa agatcgactc cgaatccact     120
tccagagttt tcaggaaga accagtcact tcgatcttga cacgttacga acctatgtc      180 gccccaatta tattcacgtt gttgtccttt tcactcgta tgtacaaaat tgggatcaac     240
aaccacgtcg tttgggatga agctcacttc ggaaagtttg gctcctacta tctcagacac     300
gagttctacc acgatgtcca ccctccgttg ggtaagatgt tggtcggtct atctggctac     360
attgccggtt acaatggctc ctgggatttc ccctccggtc aagagtaccc tgactatatt     420
gattacgtta aaatgaggtt attcaatgcc accttcagtg ccttatgtgt gccattcgcc     480 tatttccacca tgaaggagat tggatttgat atcaagacaa cttggctatt cacactgatg     540
gtcttgtgtg aaacaagtta ttgtacgtta ggaaaattca tcttgctgga ttcaatgctg     600
ctgctattca ctgtgactac ggttttcacc tttgttaggt tccataacga aaacagtaaa     660
ccaggaaact cgttttctcg caaatggtgg aaatggcttc tgcttactgg tatttccatt     720
ggtctcactt gttccgtcaa aatggtgggt ttatttgtca cagtattagt tggaatttac     780
acagttgttg acttatggaa taaatttggt gatcaatcca tttctcgtaa gaaatatgct     840
gctcattggc tagctcgttt catcggcttg attgccatcc caattggcgt ttttctattg     900
tcattccgta tccatttga aatattatcc aattctggta ccggtgatgc aaacatgtct     960
tcattgttcc aagctaacct tcgtggatca tccgtcggag gaggcccag agatgtgacc    1020 actctcaact ctaaagtgac cataaagagc caaggtttag gatctggtct agatcttaat    1080
```

-continued

| | |
|---|---|
| aggttacatt cccacgttca aacttatcct caaggttcca gccaacaaca gattacaacc | 1140 |
| tattctcaca aagatgccaa caatgattgg gtgtttcaac ttacgagaga agactctcga | 1200 |
| aacgctttca aggaagccca ctatgtcgtt gatggtatgt ctgttcgtct cgttcattca | 1260 |
| aacactggta gaaacttaca cactcaccaa gttgctgctc ccgtctcctc atccgaatgg | 1320 |
| gaagtcagtt gttatggtaa tgaaaccatt ggagacccga agataattg gattgttgaa | 1380 |
| attgtcgacc agtatggtga tgaagataag ctgagattgc acccattgac ctccagtttc | 1440 |
| cgtttgaaat cggcaactct gggatgctat ttgggtactt cgggtgcttc actgcctcaa | 1500 |
| tggggtttca gacaaggtga agttgtttgt tacaaaaatc cgttccgtag agataagcgc | 1560 |
| acctggtgga acatcgagga cggatcccat aacaatcctg atctacctaa tcctccagaa | 1620 |
| aattttgttc ttcccaggac tcatttttg aaagactttg ttcaattaaa tttagcaatg | 1680 |
| atggcaacaa caacgctttt ggtcccagac ccagataagg aagataatct agcttcttct | 1740 |
| gcctgggaat ggcccacgct acacgttggt atccgtctgt gcggttgggg cgatgacaac | 1800 |
| gtcaagtatt tcttgattgg ttctcccgca accacctgga cttcttcagt tggtattgta | 1860 |
| gtattcctgt tcctgctgtt aatttacttg atcaaatggc aacgtcaata tgtcattttc | 1920 |
| ccatccgtcc agactccact agagtcagcc gacaccaaaa cagttgcatt gtttgacaag | 1980 |
| tctgatagct tcaacgtctt ccttatggga ggattatacc cgcttctggg atggggttta | 2040 |
| cattttgctc cgtttgtgat catgtcgcgt gttacctacg ttcaccatta tcttcctgca | 2100 |
| ttgtactttg ccatgattgt tttctgctac ttggtttctc tgttggataa gaaactaggc | 2160 |
| cacccagcat taggattact gatctatgtg gctctgtatt ccttggtcat tggaacattt | 2220 |
| atttggctca gccccgttgt gtttggtatg gacggtccga acagaaatta cagttaccta | 2280 |
| aaccttctac ctagttggag agtatcagac ccatag | 2316 |

<210> SEQ ID NO 3
<211> LENGTH: 1725
<212> TYPE: DNA
<213> ORGANISM: Pichia pastoris
<220> FEATURE:
<221> NAME/KEY: gene
<222> LOCATION: (1)..(1725)

<400> SEQUENCE: 3

| | |
|---|---|
| atgataaaat caagaaagag atcgagaaaa gtttctttga cactgaaaaa ggagctgaaa | 60 |
| aatagccata tttctcttgg agatgaaaga tggtacactg tgggtcttct cttggtgaca | 120 |
| atcacagctt tctgtactcg attctatgct atcaactatc cagatgaggt tgttttgac | 180 |
| gaagttcatt tcggaaaatt tgctagctac tatctagagc gtacttattt ttttgatctg | 240 |
| caccctccgt ttgccaagct cctgattgcg tttgtcggct ttttagctgg gtacaatggt | 300 |
| gagttcaagt ttacaactat tggtgaatct tatatcaaaa acgaggttcc ctacgtagtt | 360 |
| tacagatcat tgagcgctgt gcaaggatct ttaacggtgc caattgttta tttgtgtctc | 420 |
| aaagaatgcg gatatacagt tttgacttgt gtttttggtg catgtatcat attgtttgat | 480 |
| ggggcccacg ttgctgagac tagactaatc ttgctggatg ccacgttgat tttttcgtt | 540 |
| tcattgtcca tctatagcta tatcaaattc acaaaacaaa gatcagaacc attcggccaa | 600 |
| aagtggtgga agtggctgtt ctttacaggg gtgtctttat cttgcgtcat aagtaccaag | 660 |
| tatgtggggg tgttcaccta tcttacaata ggctgtggtg tcctgtttga cttatggagt | 720 |
| ttactggatt ataaaagggg acattccttg gcatatgttg gtaaacactt tgctgcacga | 780 |
| ttttccttc taatactggt cccttcttg atatatctca attggtttta tgttcatttc | 840 |

```
gctattctaa gcaagtctgg cccaggagac agttttatga gctctgaatt ccaggagact    900
ctcggagatt ctcctcttgc agctttcgca aaggaagttc actttaacga cataatcaca    960
ataaagcata aagagactga tgccatgttg cactcacact tggcaaacta ccccctccgt   1020
tacgaggacg ggagggtatc atctcaaggt caacaagtta cagcatactc tggagaggac   1080
ccaaacaata attggcagat tatttctccc gaaggactta ctggcgttgt aactcagggc   1140
gatgtcgtta gactgagaca cgttgggaca gatggctatc tactgacgca tgatgttgcg   1200
tctcctttct atccaactaa cgaggagttt actgtagtgg gacaggagaa agctactcaa   1260
cgctggaacg aaacactttt tagaattgat ccctatgaca agaagaaaac ccgtcctttg   1320
aagtcgaaag cttcattttt caaactcatt catgttccta cggttgtggc catgtggact   1380
cataatgacc agcttcttcc tgattggggt ttcaaccaac aagaagtcaa tggtaataag   1440
aagcttgctg atgaatcaaa cttatggggt gtagacaata tcgtcgatat tgcagaggac   1500
gatccaagga aacactacgt tccaaaggaa gtgaaaaatt tgccattttt gaccaagtgg   1560
ttggaattac aaagacttat gtttattcag aataacaagt tgagctcaga tcatccattt   1620
gcgtctgacc ctatatcttg gccttttcca cttagtgggg tttcattttg gacaaacaac   1680
gagtcacgca aacagatcta ttttgtcgga aatattcctg gatgg              1725
```

<210> SEQ ID NO 4
<211> LENGTH: 1278
<212> TYPE: DNA
<213> ORGANISM: Pichia pastoris
<220> FEATURE:
<221> NAME/KEY: gene
<222> LOCATION: (1)..(1278)
<220> FEATURE:
<221> NAME/KEY: misc_feature
<222> LOCATION: (952)..(952)
<223> OTHER INFORMATION: n is a, c, g, or t

<400> SEQUENCE: 4

```
atggccgcct ttgagtacaa aaagggcatt caaagaccct attttttac caagccattg      60 gtgaaaccta taacgctaag cggctttgaa aaaatacaat tggctttgtt tcttgcgttc    120
acagtggccg tgagattctt caatattcaa taccccaacc aaattgtatt tgatgaggtc    180
cattttggaa aatatgcccg aaactacatc aatagctcat acttcatgga tgtgcaccct    240
cctttagtca agatgcttta cgccgccata ggctatttag gtggttacag aggagatttt    300
gttttcaaca agattgggga taactacatt ggtaaagagg gtgaaaaatt ggtaccctac    360
gttttgatgc gatcgtttcc cgcaatttgt ggagtcttga ttgttattct ttcttacttt    420
atccttagat acagcggatg ccgacatttt attgcacttt ttggagcttt actggtttgt    480
attgaaaact cattggtagc tcaatcaaga tttattctac tagattctcc attgctttta    540
ttcattgttc tcacagtata cagttttgtg agattcagca atgaaccaga accttttggc    600
aaaggctgga taagatatct atttttcact ggtgtgtcct tgggactcag tgtcagtagt    660
aaatgggttg aatattcac aattggttgg ttaggagtca tgactgtaaa ccaattgtgg    720
tggttaattg gagacttaag cgttcccgat cgtgatgtgg taaagcatgt cttgtacaga    780
gcgtattttc ttattatcct accagtgatc atttaccttg gggtgttttgc aatccatttt    840 ttggttctcc atgaagctag tggctggttc agtgtacatg tgagtcctat gattcaaatg    900
ccatgtttgg acgtgaactt gattttttcca atccttatg ctaactgtgt cnttttggat    960
ccacctgttt cgataagaca ccttggtaca ggagagtttc tacactccca caaccacaca   1020
```

-continued

| | |
|---|---|
| tatcctaaat cgcacaacca acaggtaacc ctatacggat acaaagactc caataatctt | 1080 |
| ttcactattt gaaaagaaag aaaagctatc tggacaggga ctattctcgg agatgtattc | 1140 |
| tccctcagac agaagatgat gttaataaga ttatttcaca aaaaaaccga ggatatgagg | 1200 |
| acgtgtctga ttctagacct tccaattagt gaagatctgc aagagtacaa caatgagttc | 1260 |
| agtattatag gagactaa | 1278 |

<210> SEQ ID NO 5
<211> LENGTH: 2259
<212> TYPE: DNA
<213> ORGANISM: Pichia pastoris
<220> FEATURE:
<221> NAME/KEY: gene
<222> LOCATION: (1)..(2259)

<400> SEQUENCE: 5

| | |
|---|---|
| atggcaacag aggaagagag aaatgaactg agaagtcgga tggacgccaa taattcaaaa | 60 |
| gtttccacgt tcactacgaa caattcagat gatccttctg ttgatagcca gggtaaggtg | 120 |
| aaaattaagt catgggtttg gagccttgaa tctttaattg gccctctggt gatcactgcc | 180 |
| ttggcaattt tcttcgagt ttaccaaata ggaaaagctg atagggttgt ttgggatgaa | 240 |
| gctcatttcg gaaagtttgg gtcattctac ttgaagcacc agttctattt tgatgtccat | 300 |
| cctcccctgg gaaaacttct tacaggtttg gctgggcaca tagctggcta taatgggtcg | 360 |
| tttgagttca gagtgggggt gacgtatcca gaatatctcg atttcaaggt aatgaggata | 420 |
| ttcaatgctg ttttcagtgc actttgtgcc cctgtggcat attggactgc aaatcatgt | 480 |
| ggatattctc tactcacggt ttaccttata tcattgatgg tagtttttga aaactcctac | 540 |
| gttgttttgg ggaagtttat tctgttggat tccatgcttt tgtttttcac cacaacaacc | 600 |
| tttctgggtt tatcaaaagt tcattcattg agacagcaag gaaaagaatt aacttacccg | 660 |
| tggtgcttct ggttgacctt tacaggttta tctattggat gtgtatgcag tgtcaaactt | 720 |
| gttggactgt tcgtaactgc ccttgtgggt ctttataccaa ttcttgacct tgccgttaag | 780 |
| agatacgatg aaaaccttaa atggtctaag tacttgactc attgggcagt gcgcattcta | 840 |
| acgttgatta ttctaccgtt tgccatctac atgttatcct ttaagatcca ttttgctgtg | 900 |
| ctttacaaga atgagatgg tgcttcttca atgtcaactc tgttccaatc caatttggag | 960 |
| ggaacaaaaa ttctaattga tgcccctaga gatgttgcat atggatctga acttacaata | 1020 |
| agatcccaag gccttccca aaatcttttg cactcccatg ggtcaattta tcccgaagga | 1080 |
| tctaaccaac aacaagttac aacctacggt catagagaca ataataacca atggattgtt | 1140 |
| cattacccg tcctcagcaa gaagcaagtt aagaaaatg ataactcaac agttccagag | 1200 |
| atgatgaaag atggtgacac cattcgttta agacatcaac atactggtgc aaacttgcat | 1260 |
| tctcacagaa ttcaagctca tgttagtaaa caatactacg aagtatcatg ttacggaaat | 1320 |
| gcaaaagttt cagacggaaa cgatgagtgg gttgtggaag ttgcagagca aattcattcc | 1380 |
| gatgacccta atatgccgc tgccaacgaa tcagatttaa aattccagga actgcttcac | 1440 |
| cctatatcta cttccttcag acttcgtcat aagagaattg gatgttactt ggccactact | 1500 |
| gggatggcat atccaagctg gggtttcaag cagggtgaag tagtctgccg accatcttgg | 1560 |
| acctcaaggg acaaatctac gtggtggaac atcgaggacc ataagaacaa aaagctgcca | 1620 |
| aatgctactt catataaagc tccaaaatct tacttctgga gagactttgt catgctgaac | 1680 |
| tatgcgatgt tagcatccaa taacgcctta gtgcctgatc ctgataaatt cgataaactg | 1740 |
| gcttctcaat ggtggcaatg gcctatcatt aatgttggac tccgaatgtg tggttggagc | 1800 |

```
gcctcacaat ctagatactt cttgatgagt agcccattta atacttggtt gtcaactgct      1860
tctttggctg ttttttgctt gattgttctt attttagtcc tacaatggca aagacaaaga      1920
ctcaatctct cttctagaca gtactgggag ctagtcatca agggttttgt cccattttt       1980 ggttgggcgt tgcattttgc tccattcatt gtgatgcaaa gggtcacata cgtgcaccat      2040
tatgttcccg ctctctactt tgccatgttc ctgctgggat ttactgtaga ctatttgaca      2100
gccaagagga actgctacat caaaacattg atctattttg tcttttatgc gggcactatc      2160
tactctttct actactttc acctctcagt tttggcatgg atggcccttt aaaaaattat       2220
gcgtacttgc aatggttcaa gagttggacc atggtttga                             2259

<210> SEQ ID NO 6
<211> LENGTH: 459
<212> TYPE: DNA
<213> ORGANISM: Pichia pastoris
<220> FEATURE:
<221> NAME/KEY: gene
<222> LOCATION: (1)..(459)

<400> SEQUENCE: 6
cccactctga tctacctcac tttctttgcc atccatttgc aagtcttaac caaggaaggt        60
gatggtggtg ctttcatgtc ttccgtcttc agatcgacct tagaaggtaa tgctgttcca       120
aaacagtcgc tggccaacgt tggtttgggc tctttagtca ctatccgtca tttgaacacc       180
agaggtggtt acttacactc tcacaatcat ctttacgagg gtggtctctgg tcaacagcag      240 gtcaccttgt acccacacat tgattctaat aatcaatgga ttgtacagga ttacaacgcg      300
actgaggagc caactgaatt tgttccattg aaagacggtg tccaaatcag attaaaccac      360
aaattgactt cccgaagatt gcactctcat aacctcagac cctcctgtga tgaacaagat     420
tggcaaaatg aggtatctgc ttatggacat gagggcttt                             459

<210> SEQ ID NO 7
<211> LENGTH: 499
<212> TYPE: DNA
<213> ORGANISM: Pichia pastoris
<220> FEATURE:
<221> NAME/KEY: gene
<222> LOCATION: (1)..(499)

<400> SEQUENCE: 7
gttacattcc cacgttcaaa cttatcctca aggttccagc caacaacaga ttacaaccta       60
ttctcacaaa gatgccaaca atgattgggt gtttcaactt acgagagaag actctcgaaa      120
cgctttcaag gaagcccact atgtcgttga tggtatgtct gttcgtctcg ttcattcaaa      180
cactggtaga aacttacaca ctcaccaagt tgctgctccc gtctcctcat ccgaatggga      240
agtcagttgt tatggtaatg aaaccattgg agacccgaaa gataattgga ttgttgaaat      300
tgtcgaccag tatggtgatg aagataagct gagattgcac ccattgacct ccagtttccg      360
tttgaaatcg gcaactctgg gatgctattt gggtacttcg ggtgcttcac tgcctcaatg      420
gggtttcaga caaggtgaag ttgtttgtta caaaaatccg ttccgtagag ataagcgcac      480
ctggtggaac atcgaggac                                                   499

<210> SEQ ID NO 8
<211> LENGTH: 498
<212> TYPE: DNA
<213> ORGANISM: Pichia pastoris
<220> FEATURE:
<221> NAME/KEY: gene
```

```
<222> LOCATION: (1)..(498)

<400> SEQUENCE: 8
gttcatttcg ctattctaag caagtctggc ccaggagaca gttttatgag ctctgaattc      60
caggagactc tcggagattc tcctcttgca gctttcgcaa aggaagttca ctttaacgac     120
ataatcacaa taaagcataa agagactgat gccatgttgc actcacactt ggcaaactac     180
cccctccgtt acgaggacgg gagggtatca tctcaaggtc aacaagttac agcatactct     240
ggagaggacc caaacaataa ttggcagatt atttctcccg aaggacttac tggcgttgta     300
actcagggcg atgtcgttag actgagacac gttgggacag atggctatct actgacgcat     360
gatgttgcgt ctccttttcta tccaactaac gaggagttta ctgtagtggg acaggagaaa     420
gctactcaac gctggaacga aacactttt agaattgatc cctatgacaa gaagaaaacc     480
cgtcctttga agtcgaaa                                                   498

<210> SEQ ID NO 9
<211> LENGTH: 437
<212> TYPE: DNA
<213> ORGANISM: Pichia pastoris
<220> FEATURE:
<221> NAME/KEY: gene
<222> LOCATION: (1)..(437)
<220> FEATURE:
<221> NAME/KEY: misc_feature
<222> LOCATION: (157)..(157)
<223> OTHER INFORMATION: n is a, c, g, or t

<400> SEQUENCE: 9
atcctaccag tgatcattta ccttggggtg tttgcaatcc attttttggt tctccatgaa      60
gctagtggct ggttcagtgt acatgtgagt cctatgattc aaatgccatg tttggacgtg     120
aacttgattt ttccaatcct ttatgctaac tgtgtcnttt tggatccacc tgtttcgata     180
agacaccttg gtacaggaga gtttctacac tcccacaacc acacatatcc taaatcgcac     240
aaccaacagg taaccctata cggatacaaa gactccaata atcttttcac tatttgaaaa     300
gaaagaaaag ctatctggac agggactatt ctcggagatg tattctcccct cagacagaag     360 atgatgttaa taagattatt tcacaaaaaa accgaggata tgaggacgtg tctgattcta     420
gaccttccaa ttagtga                                                   437

<210> SEQ ID NO 10
<211> LENGTH: 497
<212> TYPE: DNA
<213> ORGANISM: Pichia pastoris
<220> FEATURE:
<221> NAME/KEY: gene
<222> LOCATION: (1)..(497)

<400> SEQUENCE: 10
cttgccgtta agagatacga tgaaaacctt aaatggtcta agtacttgac tcattgggca      60
gtgcgcattc taacgttgat tattctaccg tttgccatct acatgttatc ctttaagatc     120
cattttgctg tgctttacaa gaatggagat ggtgcttctt caatgtcaac tctgttccaa     180
tccaatttgg agggaacaaa aattctaatt gatgccccta gagatgttgc atatggatct     240
gaacttacaa taagatccca aggccttttcc caaaatcttt tgcactccca tgggtcaatt     300
tatcccgaag gatctaacca acaacaagtt acaacctacg gtcatagaga caataataac     360
caatggattg ttcattaccc cgtcctcagc aagaagcaag ttaaagaaaa tgataactca     420
acagttccag agatgatgaa agatggtgac accattcgtt taagacatca acatactggt     480
```

```
gcaaacttgc attctca                                              497

<210> SEQ ID NO 11
<211> LENGTH: 33
<212> TYPE: DNA
<213> ORGANISM: Artificial Sequence
<220> FEATURE:
<223> OTHER INFORMATION: 5'-3' PMT1 Forward Primer (PMT1FP)
<220> FEATURE:
<221> NAME/KEY: prim_transcript
<222> LOCATION: (1)..(33)

<400> SEQUENCE: 11
ggatcctaat agcccactct gatctacctc act                            33

<210> SEQ ID NO 12
<211> LENGTH: 30
<212> TYPE: DNA
<213> ORGANISM: Artificial Sequence
<220> FEATURE:
<223> OTHER INFORMATION: 5'-3' PMT1 Reverse Primer (PMT1RP)
<220> FEATURE:
<221> NAME/KEY: prim_transcript
<222> LOCATION: (1)..(30)

<400> SEQUENCE: 12
ggatccaaag ccctcatgtc cataagcaga                                30

<210> SEQ ID NO 13
<211> LENGTH: 33
<212> TYPE: DNA
<213> ORGANISM: Artificial Sequence
<220> FEATURE:
<223> OTHER INFORMATION: 5'-3' PMT2  Forward Primer (PMT2FP)
<220> FEATURE:
<221> NAME/KEY: prim_transcript
<222> LOCATION: (1)..(33)

<400> SEQUENCE: 13
ggatcctaat aggtgggttt atttgtcaca gta                            33

<210> SEQ ID NO 14
<211> LENGTH: 29
<212> TYPE: DNA
<213> ORGANISM: Artificial Sequence
<220> FEATURE:
<223> OTHER INFORMATION: 5'-3' PMT2 Reverse Primer (PMT2RP)
<220> FEATURE:
<221> NAME/KEY: prim_transcript
<222> LOCATION: (1)..(29)

<400> SEQUENCE: 14
ggatccgaaa cacccaatca ttgttggca                                 29

<210> SEQ ID NO 15
<211> LENGTH: 34
<212> TYPE: DNA
<213> ORGANISM: Artificial Sequence
<220> FEATURE:
<223> OTHER INFORMATION: 5'-3' PMT4 Forward Primer (PMT4FP)
<220> FEATURE:
<221> NAME/KEY: prim_transcript
<222> LOCATION: (1)..(34)

<400> SEQUENCE: 15
ggatcctaat aggttcattt cgctattcta agca                           34

<210> SEQ ID NO 16
<211> LENGTH: 28
```

```
<212> TYPE: DNA
<213> ORGANISM: Artificial Sequence
<220> FEATURE:
<223> OTHER INFORMATION: 5'-3' PMT4 Reverse Primer (PMT4RP)
<220> FEATURE:
<221> NAME/KEY: prim_transcript
<222> LOCATION: (1)..(28)

<400> SEQUENCE: 16
ggatcctttc gacttcaaag gacgggtt                                        28

<210> SEQ ID NO 17
<211> LENGTH: 35
<212> TYPE: DNA
<213> ORGANISM: Artificial Sequence
<220> FEATURE:
<223> OTHER INFORMATION: 5'-3' PMT5 Forward Primer (PMT5FP)
<220> FEATURE:
<221> NAME/KEY: prim_transcript
<222> LOCATION: (1)..(35)

<400> SEQUENCE: 17
agatcttaat agatcctacc agtgatcatt tacct                                35

<210> SEQ ID NO 18
<211> LENGTH: 30
<212> TYPE: DNA
<213> ORGANISM: Artificial Sequence
<220> FEATURE:
<223> OTHER INFORMATION: 5'-3' PMT5 Reverse Primer (PMT5RP)
<220> FEATURE:
<221> NAME/KEY: prim_transcript
<222> LOCATION: (1)..(30)

<400> SEQUENCE: 18
agatcttcac taattggaag gtctagaatc                                      30

<210> SEQ ID NO 19
<211> LENGTH: 35
<212> TYPE: DNA
<213> ORGANISM: Artificial Sequence
<220> FEATURE:
<223> OTHER INFORMATION: 5'-3' PMT6 Forward Primer (PMT6FP)
<220> FEATURE:
<221> NAME/KEY: prim_transcript
<222> LOCATION: (1)..(35)

<400> SEQUENCE: 19
ggatcctaat agcttgccgt taagagatac gatga                                35

<210> SEQ ID NO 20
<211> LENGTH: 30
<212> TYPE: DNA
<213> ORGANISM: Artificial Sequence
<220> FEATURE:
<223> OTHER INFORMATION: 5'-3' PMT6 Reverse Primer (PMT6RP)
<220> FEATURE:
<221> NAME/KEY: prim_transcript
<222> LOCATION: (1)..(30)

<400> SEQUENCE: 20
ggatcctgag aatgcaagtt tgcaccagta                                      30

<210> SEQ ID NO 21
<211> LENGTH: 27
<212> TYPE: DNA
<213> ORGANISM: Artificial Sequence
<220> FEATURE:
<223> OTHER INFORMATION: 5'-3' Reverse Primer (InSTEzRP)
<220> FEATURE:
```

```
<221> NAME/KEY: prim_transcript
<222> LOCATION: (1)..(27)

<400> SEQUENCE: 21
tagcagagcg aggtatgtag gcggtgc                                        27

<210> SEQ ID NO 22
<211> LENGTH: 24
<212> TYPE: DNA
<213> ORGANISM: Artificial Sequence
<220> FEATURE:
<223> OTHER INFORMATION: 5'-3' Reverse Primer (TEFDSRP)
<220> FEATURE:
<221> NAME/KEY: prim_transcript
<222> LOCATION: (1)..(24)

<400> SEQUENCE: 22
gagtccgaga aaatctggaa gagt                                           24

<210> SEQ ID NO 23
<211> LENGTH: 27
<212> TYPE: DNA
<213> ORGANISM: Artificial Sequence
<220> FEATURE:
<223> OTHER INFORMATION: 5'-3' Forward Primer (ISCHKFP)
<220> FEATURE:
<221> NAME/KEY: prim_transcript
<222> LOCATION: (1)..(27)

<400> SEQUENCE: 23
gctacactag aaggacagta tttggta                                        27

<210> SEQ ID NO 24
<211> LENGTH: 24
<212> TYPE: DNA
<213> ORGANISM: Artificial Sequence
<220> FEATURE:
<223> OTHER INFORMATION: 5'-3' Forward Primer (SPMT1DCFP)
<220> FEATURE:
<221> NAME/KEY: prim_transcript
<222> LOCATION: (1)..(24)

<400> SEQUENCE: 24
ggacttatgg ttcatcattg gtga                                           24
```

US 8,778,659 B2

METHOD OF REDUCING GLYCOSYLATION OF PROTEINS, PROCESSES AND PROTEINS THEREOF

CROSS-REFERENCE TO RELATED APPLICATIONS

Figure 1:
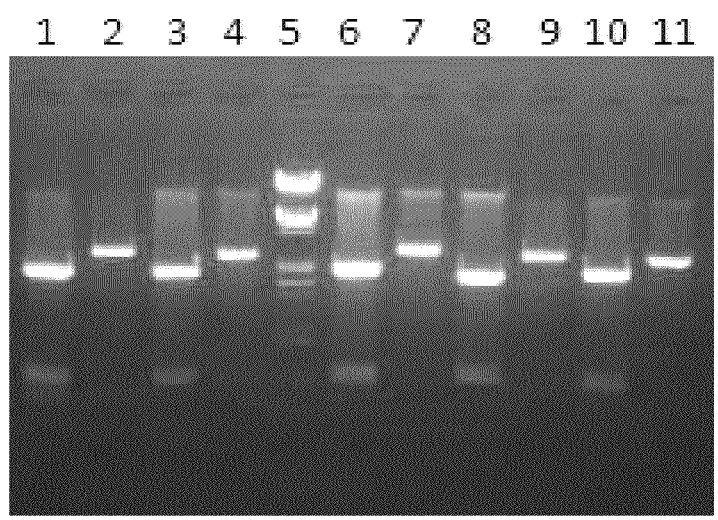

This application is a 371 U.S. National Stage of International Application No. PCT/IN2010/000190, filed Mar. 29, 2010, which claims priority to Indian Patent Application No. 332/CHE/2010, filed Feb. 10, 2010. The disclosures of the above applications are incorporated herein by reference.

TECHNICAL FIELD

The disclosure relates to disruption of Protein mannosyl transferase (PMT) genes of *Pichia pastoris* leading to reduction in the O-glycosylation levels of the insulin precursor molecule produced by *Pichia* sp. The present disclosure provides genetically engineered knock-out strains of methylotrophic yeast including *Pichia* and especially *Pichia pastoris* capable of producing heterologous proteins with reduced glycosylation. Vectors, which comprise coding sequences for PMT1, PMT2, PMT4, PMT5, and PMT6 genes, for transforming methylotrophic yeasts are contemplated by the present disclosure.

BACKGROUND OF THE DISCLOSURE

Recombinant forms of insulin, insulin analogues and/or derivatives have been produced in various microbial expression systems. Currently organisms such as *E. coli*, *S. cerevisiae* have been employed for the commercial production of recombinant human insulin and derivatives thereof. Owing to certain disadvantages of these systems such as low expression levels, difficulties in down stream purification etc., the use of methylotrophic yeast *Pichia pastoris* has been favored as a protein expression system. The expression system offers several advantages such as high expression, simple processing, low production cost, high density culture (U.S. Pat. No. 6,800,606).

Yeast expression systems are popular because they are easy to grow, are fast and scalable; however, some yeast expression systems have produced inconsistent results, and it is sometimes difficult to achieve high yields. One yeast expression system that has shown great promise is the methylotrophic yeast, *Pichia pastoris*. Compared to other eukaryotic expression systems, *Pichia* offers many advantages because it does not have the endotoxin problem associated with bacteria or the viral contamination problem of proteins produced in animal cell culture (Cino, Am Biotech Lab, May 1999).

Albeit various advantages are attributed to yeast based expression systems such as *Pichia pastoris*, one of the major disadvantages of this system is the post-translational modification of resulting proteins which later exist as impurities in the final product that is difficult to purify. Although there are a number of post translational modifications of proteins known, the most common form of post translational modification is glycosylation. (Hart G. W, Glycosylation, Curr. Opin. Cell. Biol 1992; 4: 1017). Glycosylation can be either N-linked or O-linked depending on the expression system. (Gemmill T R et al., Overview of N- and O-linked oligosaccharide structures found in various yeast species, Biochemica et Biophysica Acta, 1999; 1426:227). Glycosylation affects stability of protein conformation, immunogenicity, clearance rate, protection from proteolysis and improves protein solubility. (Walsh G, Biopharmaceutical benchmarks 2006, Nature Biotechnology, 2006; 24:769).

In yeasts, the modification of the sugar branches in the Golgi apparatus involves a series of additions of mannose residues by different mannosyl transferases ("outer chain" glycosylation). The structure of the outer chain glycosylation is specific to the organisms. Such glycosylations are often undesired since it leads to heterogeneity of a recombinant protein product in both carbohydrate composition and molecular weight, which may complicate the protein purification. It may also lead the protein to be become highly immunogenic or can provoke allergic reactions which are undesirable.

Despite great advances in improving biotechnological manufacturing, no global solutions exist for every protein. The manufacturing process for a specific therapeutic protein requires novel and innovative solutions to problems that may be specific for that protein or family of proteins.

Therefore, it is desirable to genetically engineer methylotrophic yeast strains such as *Pichia pastoris* in which glycosylation of proteins can be manipulated, essentially reduced and from which recombinant glycoproteins can be produced having a mammalian-like post translation pattern without affecting the productivity of the desired end product.

STATEMENT OF THE DISCLOSURE

Accordingly, the present disclosure relates to a method of reducing glycosylation of a protein produced from a methylotrophic yeast enabled through inactivation of at least one or more genes selected from the group comprising PMT1, PMT2, PMT4, PMT5 and PMT6 genes having a nucleotide sequence that is at least 80% homologous to nucleotide sequence represented by SEQ ID Nos. 1, 2, 3, 4 and 5 respectively, said sequences encoded for the protein mannosyl transferase or a functional part thereof; a vector containing the protein mannosyl transferase gene or a functional part thereof selected from the group comprising PMT1, PMT2, PMT4, PMT5 and PMT6 genes having a nucleotide sequence that is at least 80% homologous to nucleotide sequence represented by SEQ ID Nos. 1, 2, 3, 4 and 5 respectively, the integration of the vector into the homologous locus inhibits the expression of functional protein mannosyl transferase in a host, preferably a methylotrophic yeast; a process for the production of knock-out strain of methylotrophic yeast wherein (a) a vector incorporating a nucleic acid sequence capable of homologous recombination containing a target nucleic acid sequence encoding at least one of the genes selected from the group comprising PMT1, PMT2, PMT4, PMT5 and PMT6 having a nucleotide sequence that is at least 80% homologous to nucleotide sequence represented by SEQ ID Nos. 1, 2, 3, 4 and 5 respectively and a nucleic acid sequence coding for a selection marker (b) culturing cells under conditions to permit homologous recombination between the DNA encoding the target gene in the vector and in the host cell to occur thereby leading to disruption of the target gene in the host cell (c) selecting host cells with the inactivated target gene; a protein produced from the process described above; a knock-out strain of a methylotrophic yeast, said strain having at least one inactivated gene selected from the group comprising PMT1, PMT2, PMT4, PMT5 and PMT6 having a nucleotide sequence that is at least 80% homologous to nucleotide sequence represented by SEQ ID Nos. 1, 2, 3, 4 and 5 respectively; PMT1 genes inactivated strain as described above; PMT4 genes inactivated strain as described above; PMT5 genes inactivated strain as described above; PMT6 genes inactivated strain as described above; a protein produced from the knock-out strain as described above; a protein produced from knockout strain, wherein the knockout strain is one among MTCC 5515, MTCC 5516, MTCC 5517, MTCC 5518 or any modified strains thereof; and a protein according to any of statements above, wherein the protein exhibits modified glycosylation.

SUMMARY OF THE DISCLOSURE

The present disclosure is directed to methods of producing protein with reduced glycosylation, said method involves use of vectors that genetically modified the methylotrophic yeast strains and enable them to produce proteins with reduced glycosylation.

In a preferred embodiment, the inactivation vectors of the present disclosure include a nucleotide sequence encoding Protein mannosyl transferases (PMTs, Dolichyl-phosphate-mannose-protein mannosyltransferase proteins, E.C. 2.4.1.109) or a functional part thereof and are capable of disrupting or inactivating the protein mannosyl transferases or the functional part in a methylotrophic yeast strain. The preferred nucleotide sequences are nucleotide sequences encoding the PMT1, PMT2, PMT4, PMT5, PMT6 genes as represented in SEQ ID 1, SEQ ID 2, SEQ ID 3, SEQ ID 4, SEQ ID 5 and the functional part thereof selected for disrupting the genes as represented in SEQ ID 6, SEQ ID 7, SEQ ID 8, SEQ ID 9, SEQ ID 10 respectively.

In accordance with methods presented in the instant disclosure, a nucleotide sequence capable of expressing a heterologous protein can be introduced into a methylotrophic yeast strain which has previously been transformed with one or more of the vectors of the present disclosure in as step wise fashion. Such yeast strain can be transformed, either consecutively or simultaneously, with one or more vectors of the present disclosure. Additionally, a methylotrophic yeast strain can be transformed with one or more of the present inactivation vectors which include a nucleotide sequence encoding a protein mannosyl transferase as represented in the sequence listings.

Methylotrophic yeast strains generated using present methods and vectors, as well as proteins produced from such genetically modified strains, are also provided.

Heterologous protein products produced by using the methods of the present disclosure, i.e., proteins, with reduced O-glycosylation, are also part of the present disclosure.

According to the most significant aspects of the present disclosure, the productivity of the desired end product remains unaffected.

Additional objects and advantages of the disclosure will be set forth in part in the description which follows, and in part will be obvious from the description or may be learned from practice of the disclosure. The objects and advantages may be realized and attained by means of the instrumentalities and combinations particularly pointed out in the appended claims.

The accompanying drawings, which are incorporated herein and constitute a part of this application, illustrate various attributes useful in this disclosure and, together with the description, serve to explain the various significant attributes forming the crux of the disclosure.

BRIEF DESCRIPTION OF ACCOMPANYING FIGURES

FIG. 1: Clones obtained upon subcloning PMT genes in pPICZ alpha.

Lane 1=PMBL184 plasmid digested at BamHI and SmaI restriction enzymes (1775+576 bps fragments),
Lane 2=PMBL184 plasmid digested at BstEII restriction enzyme (linearize 2351 bps fragment),
Lane 3=PMBL185 plasmid digested at BamHI and SmaI restriction enzymes (1930+431 bps fragments)
Lane 4=PMBL185 plasmid digested at KpnI restriction enzyme (linearize 2361 bps fragment),
Lane 5=Marker, λDNA EcoRI and HindIII digest,
Lane 6=PMBL186 plasmid digested at BamHI and SmaI restriction enzymes (1923+428 bps fragments),
Lane 7=PMBL186 plasmid digested at XmnI restriction enzyme (linearize 2351 bps fragment).
Lane 8=PMBL187 plasmid digested at BamHI and SmaI restriction enzymes (1929+437 bps fragments),
Lane 9=PMBL187 plasmid digested at BstEII restriction enzyme (linearize 2366 bps fragment),
Lane 10=PMBL188 plasmid digested at BamHI and SmaI restriction enzymes (1929+497 bps fragments) and
Lane 11=PMBL188 plasmid digested at NdeI restriction enzymes (linearize 2426 bps fragment).

Figure 2A:
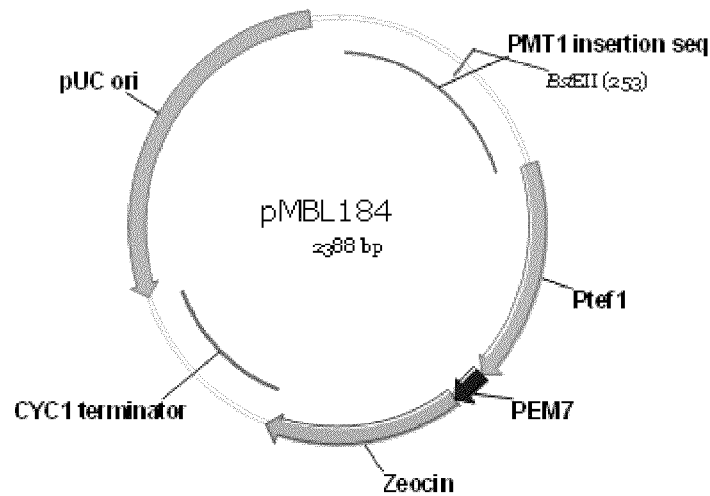
Figure 2B:
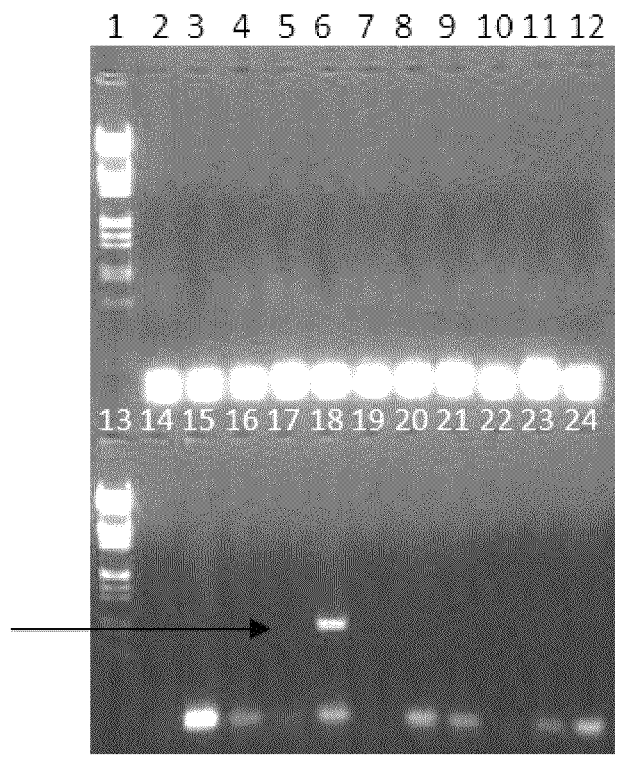
Figure 2:
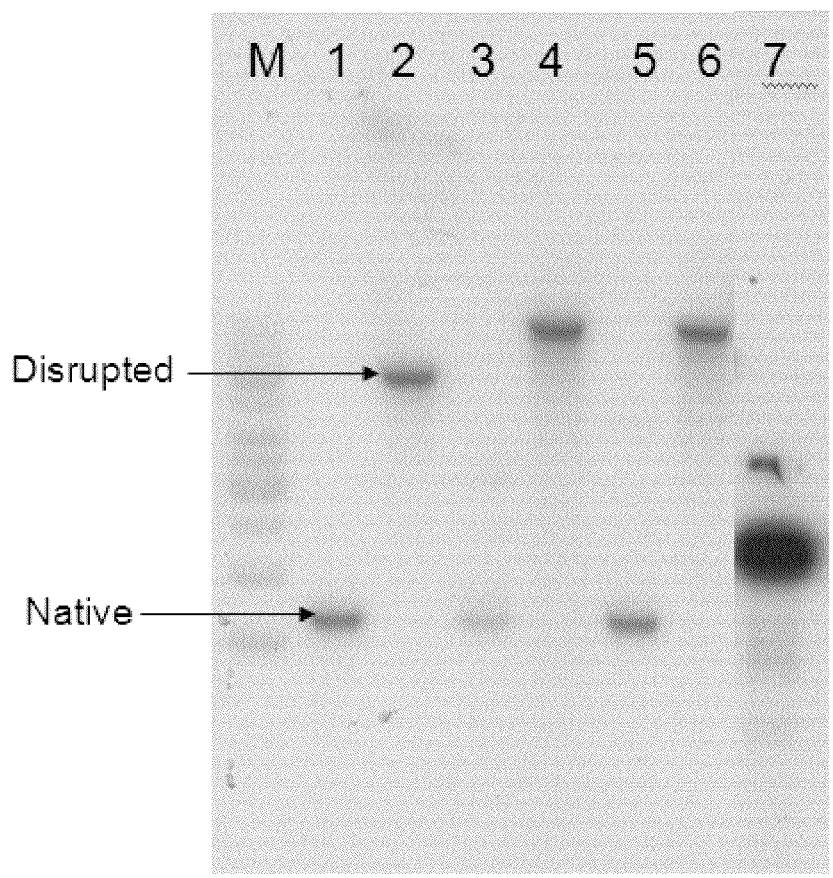

FIG. 2a: pMBL184 describes PMT1 disruption gene cloned in pPICZ alpha. BstEII restriction site used for linearising the plasmid FIG. 2b: Knock-out BICC#9104 with PMT1 gene disrupted, Lane 1 and 13=λ marker, Lane 18=BICC#9104.

FIG. 2(c): Southern Blot by digesting genomic DNA with Hind III restriction enzymes and using PMT1 disruption fragments as probe.
Lane M=1 Kb DNA marker,
Lane 1=Insulin precursor producing parent clone #11,
Lane 2=PMT1 Knock out insulin precursor producing clone #11,
Lane 3=Insulin precursor producing parent clone #8,
Lane 4=PMT1 Knock out insulin precursor producing clone of #8,
Lane 5=Insulin analog precursor producing parent clone,
Lane 6=PMT1 Knock out insulin analog precursor producing clone and Plasmid control.

Figure 3A:
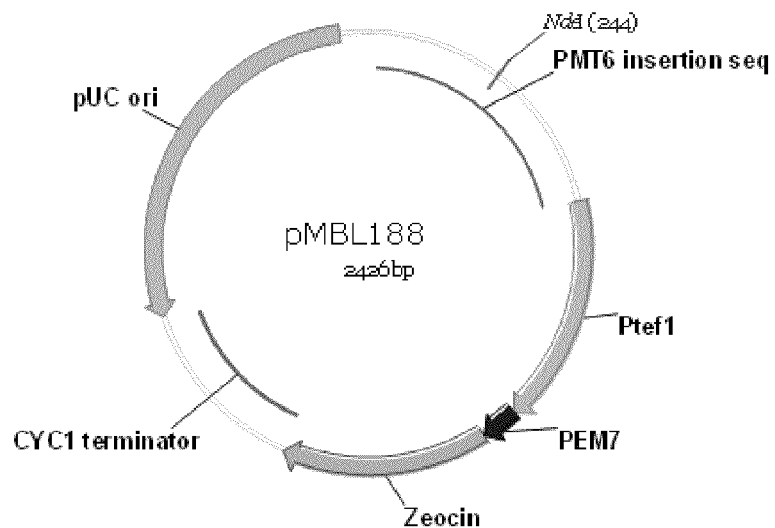
Figure 3B:
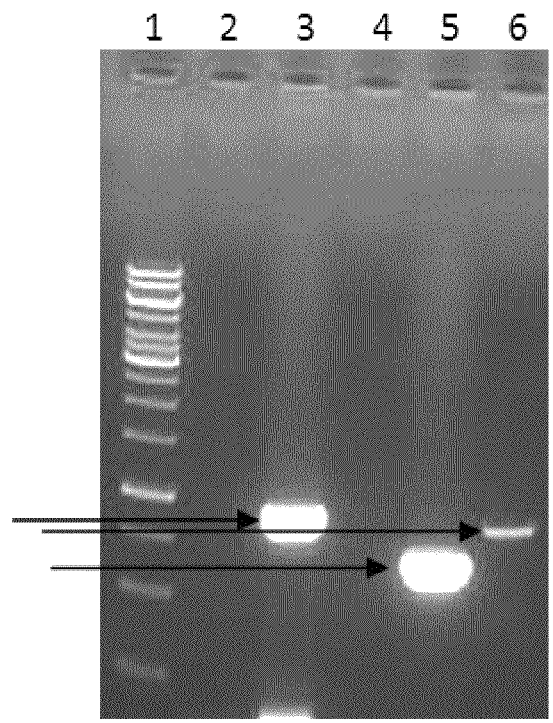

FIG. 3a: pMBL188 describes PMT6 disruption gene cloned in pPICZ alpha plasmid. NdeI restriction site was used for linearizing the plasmid FIG. 3b: PCR confirmation result of PMT6 gene knock-out
Lane 1=DNA marker, 1 kb ladder,
Lane 2=Parent clone PCR with InsteZRP and PMT6DSCHK (No product),
Lane 3=BICC#9107 PCR with InsteZRP and PMT6DSCHK (895 bp product),
Lane 4=Parent clone PCR with TEFDSRP and SPMT6DCFP (No product),
Lane 5=BICC#9107 PCR with TEFDSRP and SPMT6DCFP (639 bp product),
Lane 6=BICC#9107 PCR with ISCHKFP and PMT6DSCHK (835 bp product).

Figure 4:
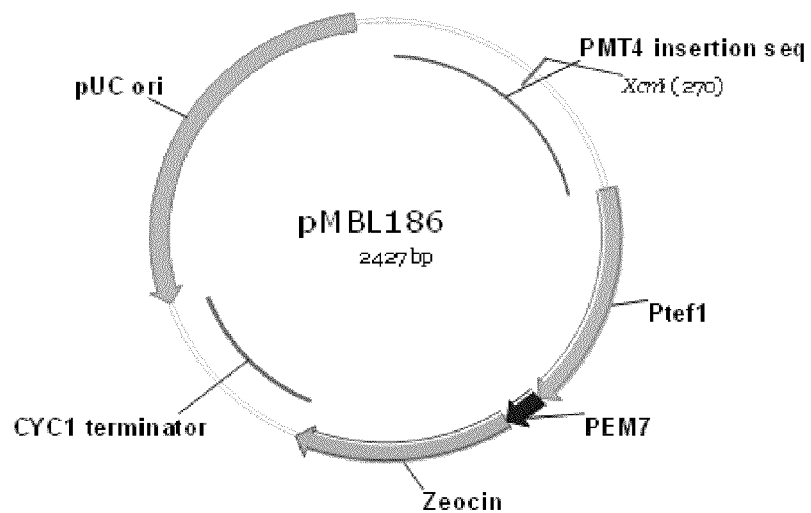
Figure 4:
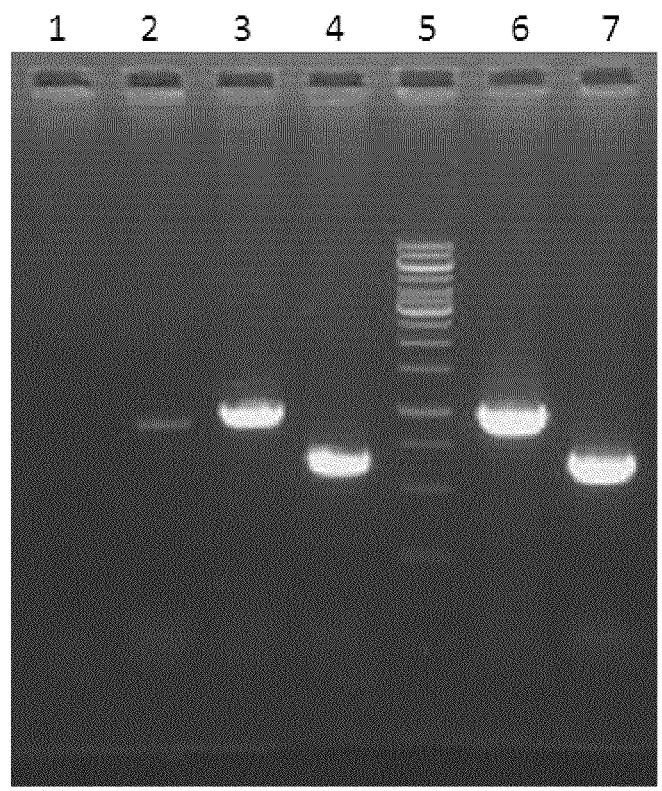

FIG. 4a: pMBL186 describes PMT4 disruption gene cloned in pPICZ alpha plasmid. XcmI restriction site was used for linearizing the plasmid.

FIG. 4b: PCR confirmation result of PMT4 gene disrupted.
Lane 1=Parent clone PCR with InsteZRP and PMT4DSCHK (No product, −ve control),
Lane 2=Positive control PMT6 #79, with InsteZRP and PMT6DSCHK (895 bp product),
Lane 3=BICC#9105 PCR with InsteZRP and PMT4DSCHK (981 bp product) (4$^{th}$ subculture), Lane 4=BICC#9105 PCR with TEFDSRP and SPMT4DCFP (649 bp product) (4$^{th}$ subculture), Lane 5=1 kb ladder DNA marker, Lane 6=BICC#9105 PCR with InsteZRP and PMT4DSCHK (981 bp product) (1st subculture), Lane 7=BICC#9105 PCR with TEFDSRP and SPMT4DRP (649 bp product) (1st subculture).

Figure 5:
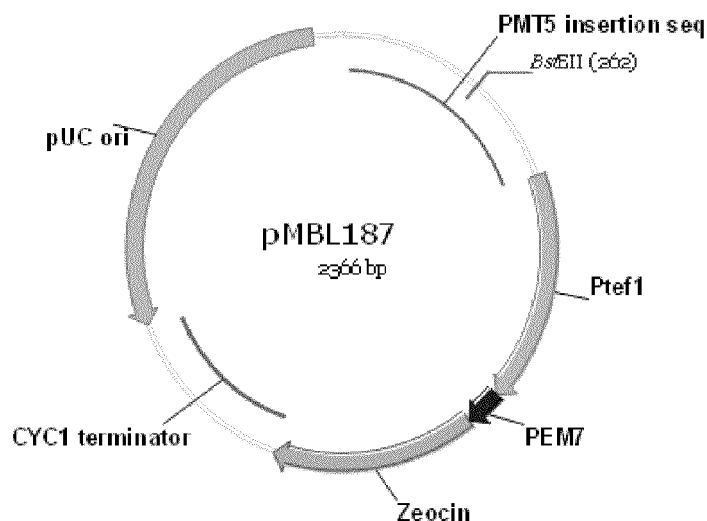
Figure 5B:
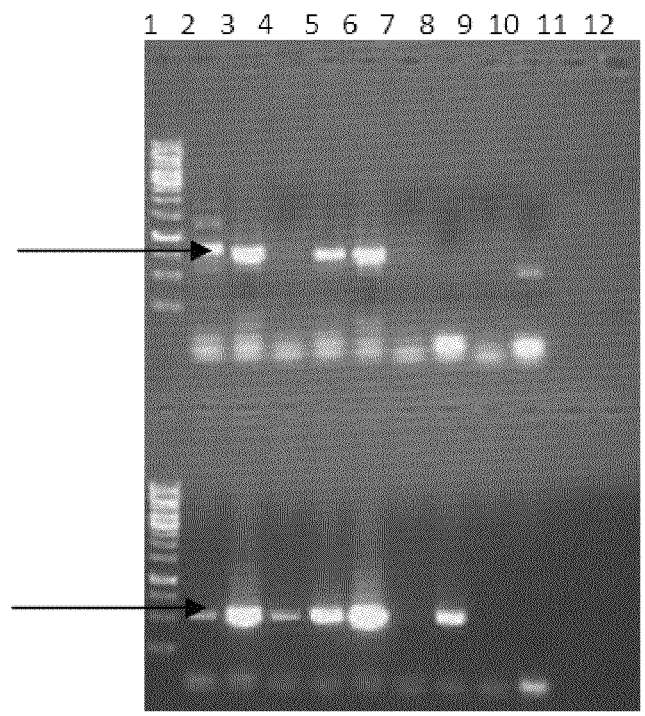

FIG. 5a: pMBL187 describes PMT5 disruption gene cloned in pPICZ alpha plasmid. BstEII restriction site was used for linearizing the plasmid FIG. 5b: PCR screening of PMT5 disrupted clones
Lane 1 and 13=DNA Molecular weight marker
Lane 2-12 and 14-21 are different PMT5 disrupted clones screened.

Figure 6A:
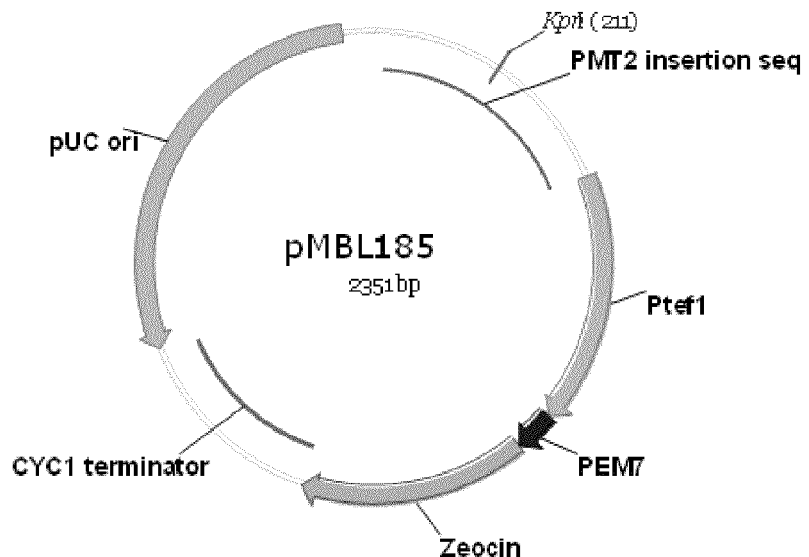
Figure 6B:
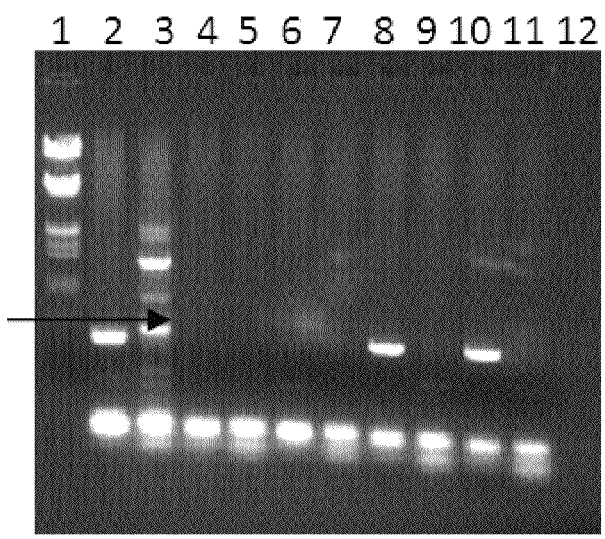

FIG. 6a: pMBL185 describes PMT2 disruption gene cloned in pPICZ alpha plasmid. KpnI restriction site was used for linearizing the plasmid FIG. 6b: PMT2 gene knock out positives screening.

Figure 7:
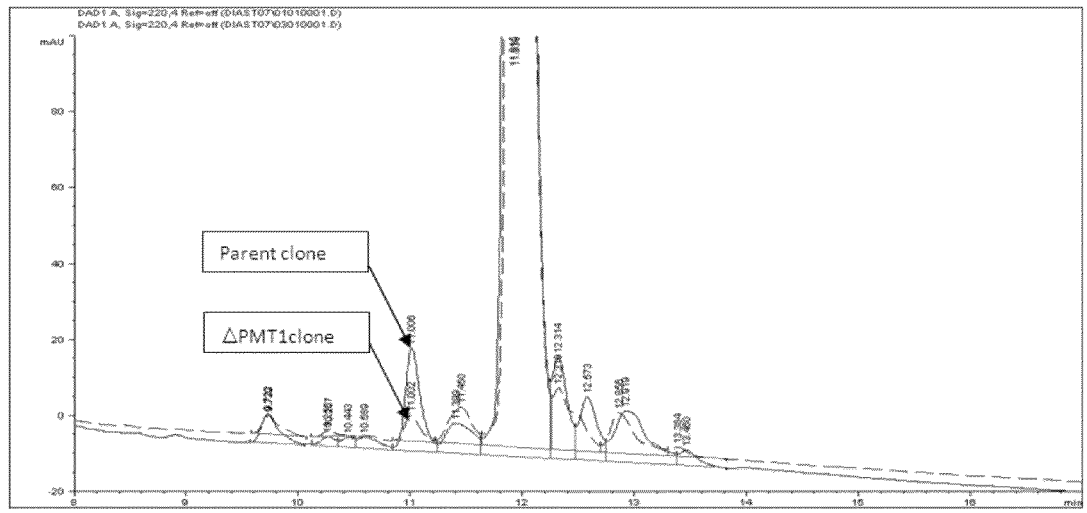

FIG. 7: Overlay of chromatogram indicating reduced glycosylation of PMT1/insulin clone.

Figure 8:
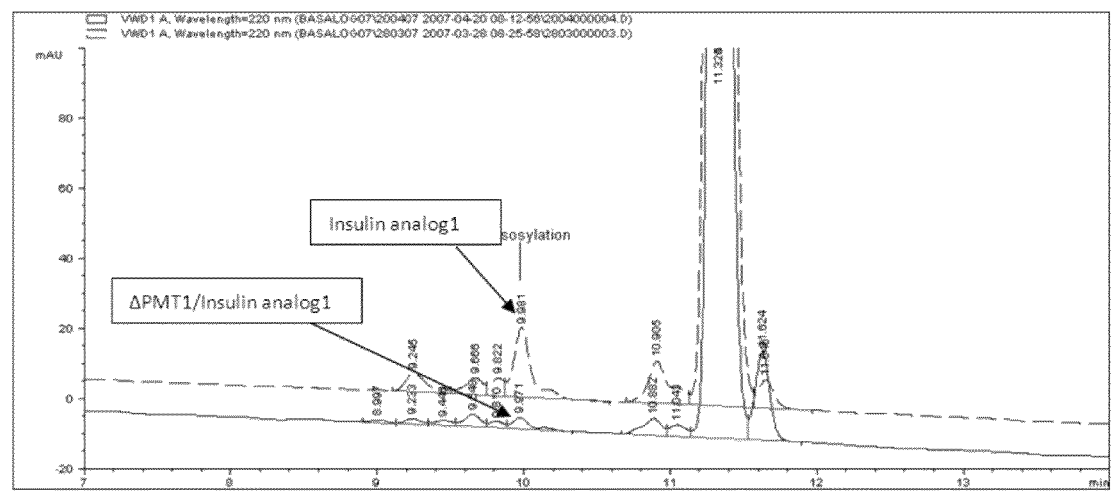

FIG. 8: RPHPLC Profile indicating Glycosylation profile with Insulin Analog 1 before and after PMT1 gene inactivation.

Figure 9:
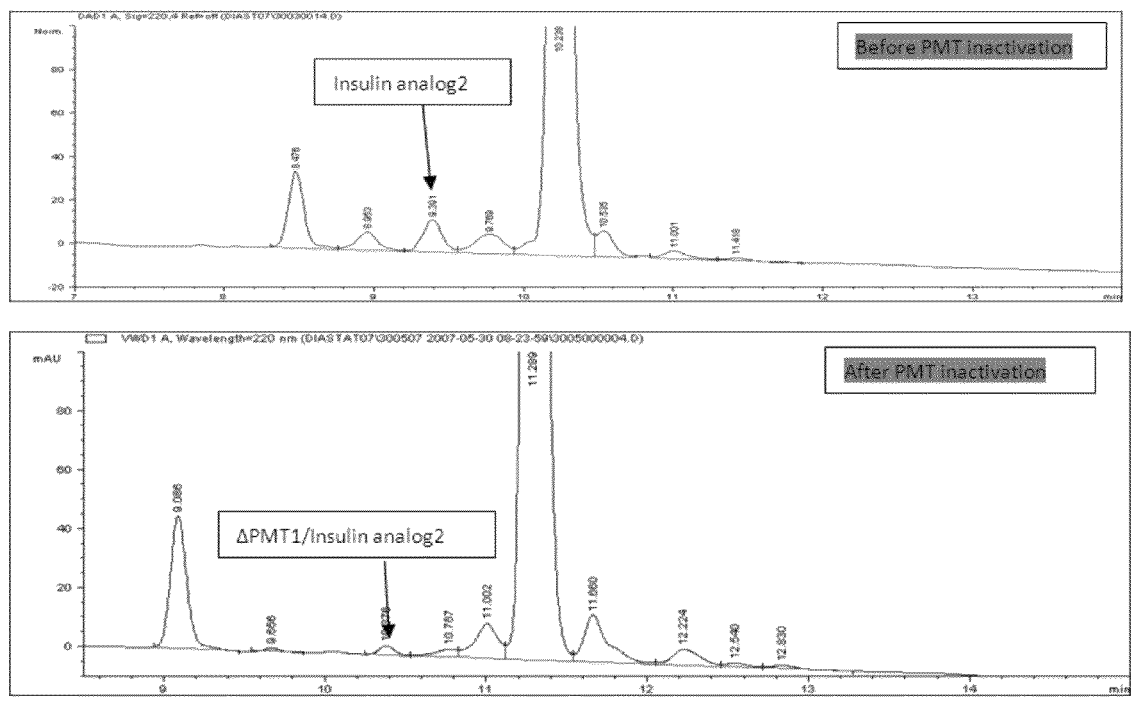

FIG. 9: RPHPLC Profile indicating Glycosylation profile with Insulin Analog 2 before and after PMT1 gene inactivation.

REPRESENTATION OF ACCOMPANYING SEQUENCE LISTINGS

SEQ ID 1: Nucleotide Coding sequence of PMT1
SEQ ID 2: Nucleotide Coding sequence of PMT2
SEQ ID 3: Nucleotide Coding sequence of PMT4
SEQ ID 4: Nucleotide Coding sequence of PMT5
SEQ ID 5: Nucleotide Coding sequence of PMT6
SEQ ID 6: Disrupted sequence of PMT1
SEQ ID 7: Disrupted sequence of PMT2
SEQ ID 8: Disrupted sequence of PMT4
SEQ ID 9: Disrupted sequence of PMT5
SEQ ID 10: Disrupted sequence of PMT6
SEQ ID 11: PMT1 Forward Primer sequence (PMT1FP)
SEQ ID 12: PMT1 Reverse Primer sequence (PMT1RP)
SEQ ID 13: PMT2 Forward Primer sequence (PMT2FP)
SEQ ID 14: PMT2 Reverse Primer sequence (PMT2RP)
SEQ ID 15: PMT4 Forward Primer sequence (PMT4FP)
SEQ ID 16: PMT4 Reverse Primer sequence (PMT4RP)
SEQ ID 17: PMT5 Forward Primer sequence (PMT5RP)
SEQ ID 18: PMT5 Reverse Primer sequence (PMT5RP)
SEQ ID 19: PMT6 Forward Primer sequence (PMT6FP)
SEQ ID 20: PMT6 Reverse Primer sequence (PMT6RP)
SEQ ID 21: Primer sequence InSTEzRP
SEQ ID 22: Primer sequence TEFDSRP
SEQ ID 23: Primer sequence ISCHKFP
SEQ ID 24: Primer sequence SPMT1DCFP

DETAILED DESCRIPTION OF THE DISCLOSURE

The present disclosure relates to a method of reducing glycosylation of a protein produced from a methylotrophic yeast enabled through inactivation of at least one or more genes selected from the group comprising PMT1, PMT2, PMT4, PMT5 and PMT6 genes having a nucleotide sequence that is at least 80% homologous to nucleotide sequence represented by SEQ ID Nos. 1, 2, 3, 4 and 5 respectively, said sequences encoded for the protein mannosyl transferase or a functional part thereof.

In an embodiment of the present disclosure, the methylotrophic yeast belongs to *Pichia* sp.

In another embodiment of the present disclosure, the methylotrophic yeast is *Pichia pastoris*.

In a further embodiment of the present disclosure, the protein is represented by formula I

X-B-Y-A wherein,
X is a leader peptide sequence comprising at least one amino acid.
B is the amino acid sequence of the B chain of the insulin molecule, its derivatives or analogs
Y is a linker peptide comprising at least one amino acid.
A is the amino acid sequence of the A chain of the insulin molecule, its derivatives or analogs
and the A and B chain can be modified by amino acid substitution, deletion and/or additions.

In another embodiment of the present disclosure, the mode of glycosylation is O-glycosylation.

In yet another embodiment of the present disclosure, the glycosylation is reduced by at least 10% to about 99%

In still another embodiment of the present disclosure, the glycosylation is reduced by 25%.

In still another embodiment of the present disclosure, the glycosylation is reduced by 65%.

The present disclosure relates to A vector containing the protein mannosyl transferase gene or a functional part thereof selected from the group comprising PMT1, PMT2, PMT4, PMT5 and PMT6 genes having a nucleotide sequence that is at least 80% homologous to nucleotide sequence represented by SEQ ID Nos. 1, 2, 3, 4 and 5 respectively, the integration of the vector into the homologous locus inhibits the expression of functional protein mannosyl transferase in a host, preferably a methylotrophic yeast.

In an embodiment of the present disclosure, The method of reducing or modifying glycosylation on proteins produced from methylotrophic yeast comprising transforming said yeast with a vector as described above.

In another embodiment of the present disclosure, the methylotrophic yeast belongs to *Pichia* sp.

In yet another embodiment of the present disclosure, the methylotrophic yeast is *Pichia pastoris*.

The present disclosure relates to a process for the production of knock-out strain of methylotrophic yeast wherein (a) a vector incorporating a nucleic acid sequence capable of homologous recombination containing a target nucleic acid sequence encoding at least one of the genes selected from the group comprising PMT1, PMT2, PMT4, PMT5 and PMT6 having a nucleotide sequence that is at least 80% homologous to nucleotide sequence represented by SEQ ID Nos. 1, 2, 3, 4 and 5 respectively and a nucleic acid sequence coding for a selection marker (b) culturing cells under conditions to permit homologous recombination between the DNA encoding the target gene in the vector and in the host cell to occur thereby leading to disruption of the target gene in the host cell (c) selecting host cells with the inactivated target gene.

The present disclosure further relates to a protein produced from the process according to any of the said preceding claims.

The present disclosure further relates to a knock-out strain of a methylotrophic yeast, said strain having at least one inactivated gene selected from the group comprising PMT1, PMT2, PMT4, PMT5 and PMT6 having a nucleotide sequence that is at least 80% homologous to nucleotide sequence represented by SEQ ID Nos. 1, 2, 3, 4 and 5 respectively.

The present disclosure relates to PMT1 genes inactivated strain as described above, having Accession number MTCC5515

The present disclosure further relates to PMT4 genes inactivated strain as described above, having Accession number MTCC5516

The present disclosure relates to PMT5 genes inactivated strain as described above, having Accession number MTCC5517

The present disclosure further relates to PMT6 genes inactivated strain as described above, having Accession number MTCC5518

In an embodiment of the present disclosure, the host strain yields protein with reduced level of glycosylation compared to protein product expressed in an unaltered host strain.

In yet another embodiment of the present disclosure, the glycosylation is reduced by at least 25%.

In still another embodiment of the present disclosure, the glycosylation is reduced by at least 65%.

The present disclosure relates to a protein produced from the knock-out strain as described above.

The present disclosure relates to a protein produced from knockout strain wherein the knockout strain is one among MTCC 5515, MTCC 5516, MTCC 5517, MTCC 5518 or any modified strains thereof.

In an embodiment of the present disclosure, the selection marker is zeocin resistance marker.

In another embodiment of the present disclosure, the protein is an insulin/insulin analogs/insulin precursor molecule.

In still another embodiment of the present disclosure, the protein produced is a heterologous protein product.

In still another embodiment of the present disclosure, the protein exhibits modified glycosylation.

In still another embodiment of the present disclosure, the productivity of the desired protein end product remains unaffected.

Reference will now be made in detail to the presently preferred embodiments of the disclosure which, together with the following example, serve to explain the principles of the disclosure.

The Examples which follow are set forth to aid in understanding the disclosure but are not intended to, and should not be construed to, limit its scope in any way. The Examples do not include detailed descriptions for conventional methods employed in the construction of vectors, the insertion of genes encoding polypeptides into such vectors or the introduction of the resulting plasmids into hosts. The Examples also do not include detailed description for conventional methods employed for assaying the polypeptides produced by such host vector systems. Such methods are well known to those of ordinary skill in the art and are described in numerous publications including by way of examples.

Standard techniques are used for various recombinant DNA techniques, transformation (e.g., electroporation, lipofection) and assays. The recombination techniques and procedures are generally performed according to conventional methods well known in the art and as described in various general and more specific references that are cited and discussed throughout the present specification. See e.g., Sambrook et al. Molecular Cloning: A Laboratory Manual (3rd ed., Cold Spring Harbor Laboratory Press, Cold Spring Harbor, N.Y. (2001)), which is incorporated herein by reference.

In describing and claiming the present disclosure, the following terminology will be used in accordance with the definitions set out herein.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The methods and techniques of the present disclosure are generally performed according to conventional methods well known in the art. Generally, nomenclatures used in connection with, and techniques of molecular and cellular biology, biochemistry, protein and nucleic acid chemistry and hybridization described herein are those well known and commonly used in the art. The methods and techniques of the present disclosure are generally performed according to conventional methods well known in the art.

As used herein "amino acid" refers to peptide or protein sequences or portions thereof. The terms "protein", "peptide" and "polypeptide" are used interchangeably.

Heterologous protein according to preferred embodiments of the disclosure is an insulin or insulin analog precursor molecule.

The DNA encoding a heterologous protein as represented by formula I

X-B-Y-A wherein,

X is a leader peptide sequence comprising at least one amino acid.

B is the amino acid sequence of the B chain of the insulin molecule, its derivatives or analogs Y is a linker peptide comprising at least one amino acid.

A is the amino acid sequence of the A chain of the insulin molecule, its derivatives or analogs and the A and B chain can be modified by amino acid substitution, deletion and/or additions.

The term "C-peptide" or "linker peptide" as used herein includes all forms of insulin C-peptide, including native or synthetic peptides. Such insulin C-peptides may be human peptides, or may be from other animal species and genera, preferably mammals. Thus variants and modifications of native insulin C-peptide are included as long as they retain insulin C-peptide activity. It is known in the art to modify the sequences of proteins or peptides, whilst retaining their useful activity and this may be achieved using techniques which are standard in the art and widely described in the literature e.g. random or site-directed mutagenesis, cleavage and ligation of nucleic acids etc. Thus, functionally equivalent variants or derivatives of native insulin C-peptide sequences may readily be prepared according to techniques well known in the art, and include peptide sequences having a functional, e.g. a biological, activity of a native insulin C-peptide. All such analogues, variants, derivatives or fragments of insulin C-peptide are especially included in the scope of this disclosure, and are subsumed under the term "an insulin C-peptide".

The linker sequence can be any sequence having at least two amino acids The linker region may comprise from 2 to 25, 2 to 15, 2 to 12 or 2 to 10 amino residues, although the length is not critical and may be selected for convenience or according to choice or it can be without a linker.

The linker peptide may be any sequence comprising at least two amino acids under the provision that the first two amino acids represent "RR".

Polypeptides according to yet other embodiments of the disclosures are referred to herein as possessing the activity of insulin glargine, e.g. are insulin glargine are understood to have an amino acid sequence with two changes of the human insulin structure: substitution of the amino acid glycine for the native asparagine at position A21 of the A-chain of human insulin and the addition of two arginine molecules to the COOH-terminal end of the B-chain of human insulin produced by recombinant DNA technology The primary action of any insulin, including insulin glargine, is regulation of glucose metabolism. Insulin and its analogs lower blood glucose levels by stimulation of peripheral glucose uptake, especially within skeletal muscle and fat, and by inhibition of hepatic glucose production.

The term "insertional inactivation" means interruption of the coding region of a gene by the insertion of exogenous DNA, leading to the loss of gene function. This is widely used in gene technology to permit easy selection of recombinants following transformation.

The term "knockout" refers to the disruption of a gene wherein the disruption results in the functional inactivation of the native gene; the deletion of the native gene or a portion thereof, or a mutation in the native gene. With specific reference to the instant disclosure "knock out" refers to the disruption of PMT1, PMT2, PMT4, PMT5, PMT6 genes.

A knock-out strain can be prepared according to any of the various methods known in the art as effective. For example, homologous recombination vectors containing homologous targeted gene sequences 5' and 3' of the desired nucleic acid deletion sequence can be transformed into the host cell. Ideally, upon homologous recombination, a desired targeted enzymatic gene knock-out can be produced.

"Homologous recombination" means the exchange of DNA fragments between two DNA molecules paired chromosomes at the site of identical or nearly identical nucleotide sequences. In homologous recombination, the incoming DNA interacts with and integrates into a site in the genome that contains a substantially homologous DNA sequence. In non-homologous ("random" or "illicit") integration, the incoming DNA integrates not at a homologous sequence in the genome but elsewhere, at one of a large number of potential locations.

For example, mutant, functional or non-functional genes, flanked by DNA homologous to the endogenous target gene (e.g., the coding regions flanking the target gene) can be used, with or without a selectable marker and/or a negative selectable marker, to transform cells encoding the undesirable form of the target gene in vivo. Insertion of the DNA construct, via targeted homologous recombination, results in inactivation of the endogenous gene.

As used herein, the term "homologous" or means either i) a protein or peptide that has an amino acid sequence that is substantially similar (i.e., at least 70, 75, 80, 85, 90, 95, or 98%) to the sequence of a given original protein or peptide and that retains a desired function of the original protein or peptide or ii) a nucleic acid that has a sequence that is substantially similar (i.e., at least 70, 75, 80, 75, 90, 95, or 98%) to the sequence of a given nucleic acid and that retains a desired function of the original nucleic acid sequence. In all of the embodiments of this disclosure and disclosure, any disclosed protein, peptide or nucleic acid can be substituted with a homologous or substantially homologous protein, peptide or nucleic acid that retains a desired function. In all of the embodiments of this disclosure and disclosure, when any nucleic acid is disclosed, it should be assumed that the disclosure also includes all nucleic acids that hybridize to the disclosed nucleic acid.

By "functional part" is meant a fragment of the PMT gene which substantially retains the enzymatic activity of the full-length protein. By "substantially" is meant that at least about 40%, or preferably, at least 50% or more of the enzymatic activity of the full-length PMT is retained.

A nucleic acid is "operably linked" when it is placed into a functional relationship with another nucleic acid sequence. Thus, a coding sequence "operably linked" to control sequences refers to a configuration wherein the coding sequence can be expressed under the control of these sequences and wherein the DNA sequences being linked are contiguous.

As used herein the term "expression" refers to a process by which a polypeptide is produced based on the nucleic acid sequence of a gene. The process includes both transcription and translation.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at lest about 97% nucleic acid sequence identity, alternatively at least about 98% nucleic acid sequence identity and alternatively at least about 99% nucleic acid sequence identity to a DNA molecule encoding a PMT1, PMT2, PMT4, PMT5, PMT6 genes.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (BLAST, FASTA, GAP, BESTFIT and TFASTA in the Wisconsin Genetics Software Package, Genetics Computer Group (GCG), 575 Science Dr., Madison, Wis.), or by inspection.

One example of algorithms that can be suitable for determining percent sequence identity and sequence similarity are the BLAST and BLAST 2.0 algorithms, which are described in Altschul et al. (1977) Nucl. Acids Res. 25:3389 3402 and Altschul et al. (1990) J. Mol. Biol. 215:403 410, respectively.

More particularly, the present disclosure is directed to a nucleic acid sequence, suitably an isolated nucleic acid sequence, which includes or comprises at least SEQ ID 1, SEQ ID 2, SEQ ID 3, SEQ ID 4, SEQ ID 5, their variants or portions thereof, or at least one of the PMT1, PMT2, PMT4, PMT5, PMT6 genes, including variants or portions. The disclosure is also directed to an isolated nucleic acid sequence capable of hybridizing under stringent conditions with these nucleic acid sequences.

The disclosure provides vectors comprising DNA encoding any of the herein described genes. Host cell comprising any such vectors are also provided. By way of example, the host cells may be bacterial, fungal, or mammalian.

The disclosure is also directed to a recombinant host cell in which at least a portion of a nucleic acid sequence as defined above is disrupted to result in a recombinant host cell that produces reduced levels of glycosylated insulin precursor relative to a corresponding parent recombinant host cell. A recombinant expression system is selected from prokaryotic and eukaryotic hosts. Eukaryotic hosts include yeast cells (e.g., *Saccharomyces cerevisiae* or *Pichia pastoris*), mammalian cells or plant cells. Bacterial and eukaryotic cells are available from a number of different sources including commercial sources to those skilled in the art, e.g., the American Type Culture Collection (ATCC; Rockville, Md.). Commercial sources of cells used for recombinant protein expression also provide instructions for usage of the cells. The choice of the expression system depends on the features desired for the expressed polypeptide.

Most preferably related to aspects to the present disclosures, the most preferred host cells are methylotrophic yeasts. Strains of a methylotrophic yeast which can be modified using the present disclosure include, but are not limited to, yeast strains capable of growing on methanol, such as yeasts of the genera *Pichia, Candida, Hansenula*, or *Torulopsis*. Preferred methylotrophic yeasts are of the genus *Pichia*. Methylotrophic yeast strains which can be modified using the present methods also include those methylotrophic yeast strains which have been engineered to express one or more heterologous proteins of interest. The glycosylation on the heterologous proteins expressed from these previously genetically engineered strains can be reduced by transforming such strains with one or more of the vectors of the present disclosure.

The host cell or organism can be engineered to express recombinant protein or peptide using standard techniques. For example, recombinant protein can be expressed from a vector or from an exogenous gene inserted into the genome of the host.

Vectors that can be used to express exogenous proteins are well known in the art and are described below. Genes for expressing recombinant protein or peptide can also be inserted into the genome using techniques such as homologous or heterologous recombination, as described in the instant disclosure. Preferred vectors of the present disclosure carrying Protein mannosyl transferase genes include but are not limited to pPICZ alpha and pTZ57R.

In another aspect, the present disclosure provides inactivation vectors which, when introduced into a methylotrophic yeast strain, inactivate or disrupt a gene thereby facilitating the reduction in the glycosylation of desired protein end products produced in the methylotrophic yeast strain without affecting the productivity of the end product.

The recombinant protein or peptide can be expressed after induction with a chemical compound or upon expression of an endogenous gene or gene product. The recombinant protein can also be expressed when the host cell is placed in a particular environment. Specific promoter elements are described below.

As used herein, the terms "transformed" and "stably transformed" refers to a cell that has been made to incorporate a non-native (heterologous) polynucleotide sequence integrated into an episomal plasmid that is maintained for at least two generations.

As used herein, "recombinant" includes reference to a cell or vector, that has been modified by the introduction of a heterologous nucleic acid sequence or that the cell is derived from a cell so modified.

Vectors may be transformed into host cells by means including, but not limited to electroporation, viral infection, calcium phosphate precipitation, DEAE-dextran, direct microinjection, DNA-loaded liposomes and lipofectamine-DNA complexes, cell sonication, gene bombardment using high velocity microprojectiles or any other means described herein or known in the art.

The disclosure is also directed to a method of producing a desired protein comprising fermenting, under conditions and in a medium suitable for producing such a protein compound or its analogue, in an organism such as *Pichia* sp, in which the genes encoding polypeptides sufficient to direct the production of the desired end product has been incorporated.

It is been found that Protein mannosyl transferase genes (PMT) catalyse the O-glycosylation of serine and threonine residues of proteins in the endoplasmic reticulum. It is has been demonstrated in the instant disclosure that disruption of PMT genes dramatically decreases the O-glycosylation levels of the insulin precursor molecule produced. Disruption of the PMT1 gene resulted in an insulin precursor showing ~65% of decrease in mannosylation. The individual disruption of PMT5 and PMT6 genes resulted in reduction of insulin precursor glycosylation levels by 31% and 28% respectively. The disruption of PMT2 and PMT4 did not affect mannosylation.

As used herein, the term "reduced expression" is broadly construed to include reduced production of a protein of interest. Reduced expression is that expression below the normal level of expression in the corresponding host strain that has not been altered according to the teachings herein but has been grown under essentially the same growth conditions. In context of the present disclosure the enzyme or protein of interest are mannosyl transferases that have a significant role to play in glycosylation of the mannose residues of the insulin/insulin analog precursor molecule.

According to one aspect of the disclosure, reduction of glycosylation may be at least 20%, preferably at least 25%, preferably at least 30%, preferably at least 35%, more preferably at least 40%, more preferably at least 45%, more preferably at least 50%, more preferably at least 55%, most preferably at least 60%, most preferably at least 65% and most preferably at least 70%. According to yet another aspect of the disclosure the reduction of glycosylation obtainable is about 100%.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH).

The technique of PCR is described in numerous publications, including, PCR: A Practical Approach, M. J. McPherson et al., IRL Press (1991), PCR Protocols: A Guide to Methods and Applications, by Innis et al.; Academic Press (1990), and PCR Technology: Principals and Applications of DNA Amplification, H. A. Erlich, Stockton Press (1989).

PCR is also described in many U.S. patents, including U.S. Pat. Nos. 4,683,195, 4,683,202; 4,800,159; 4,965,188; 4,889,818; 5,075,216; 5,079,352; 5,104,792, 5,023,171; 5,091,310; and 5,066,584, which are hereby incorporated by reference.

According to the most significant aspects of the present disclosure, process for the production of "knock-out" strains of methylotrophic yeasts wherein (a) a vector incorporating a nucleic acid sequence encoding for at least one gene selected from the group consisting PMT1, PMT2, PMT4, PMT5, and PMT6 as represented by SEQ IDs 1, 2, 3, 4 and 5 respectively and a nucleic acid sequence coding for a selectable marker (b) culturing the cells under conditions that a homologous recombination occurs thereby disrupting the target nucleic acid sequences in the host cells thereby (c) selecting the cells in which the homologous recombination has taken place and (d) assessing the level of decrease in glycosylation in the altered strains.

All transformations to *Pichia pastoris* hosts were performed with electroporation. Transformants of vectors carrying the Zeocin resistance gene were selected on YPD plates containing 100 µg/ml of Zeocin.

Thus, the methods of the instant disclosure result in an altered yeast strain capable of producing a protein of interest, wherein said strain has at least one inactivated gene selected from the group comprising PMT1, PMT2, PMT4, PMT5, and PMT6 as represented by SEQ IDs 1, 2, 3, 4 and 5 respectively and (b) growing said altered strains under conditions such that reduced level of glycosylated end products in comparison to the protein products produced in an unaltered host strain.

It is to be understood that this disclosure is not limited to the particular methodology, protocols, cell lines, vectors, species or genera, and media components described, as such may vary. It is also to be understood that the terminology used herein is for the purpose of describing particular embodiments only, and is not intended to limit the scope of the present disclosure which will be limited only by the appended claims. The above description is for the purpose of teaching the person of ordinary skill in the art how to practice the present disclosure, and it is not intended to detail all those obvious modifications and variations of it which will become apparent to the skilled worker upon reading the description.

Deposit of PMT Genes Inactivated Strains

In compliance with the requirements of full disclosure, Strains of this disclosure have been deposited in the IMTEC Institute of Microbial Technology, Sector 39-A, Chandigarh 160036, India (according to international deposition based on Budapest Treaty). The strains are (accession numbers shown in parentheses):

| Strain name | MTCC |
|---|---|
| ΔPMT1/GS115 | MTCC 5515 |
| ΔPMT4/GS115 | MTCC 5516 |
| ΔPMT5/GS115 | MTCC 5517 |
| ΔPMT6/GS115 | MTCC 5518 |

The disclosure will be more fully described and understood with reference to the following examples, which are given by way of illustration and are not intended to limit the scope of the disclosure in any way.

EXAMPLE 1

Disruption of PMT1

About ~477 bps of coding sequence involving part of the *Pichia pastoris* PMT1 coding region was amplified using following PMT1 primers

```
                                              (SEQ ID 11)
PMT1FP = 5' GGA TCC TAA TAG CCC ACT CTG ATC TAC
CTC ACT 3'

(SEQ ID 12)
PMT1RP = 5' GGA TCC AAA GCC CTC ATG TCC ATA AGC
AGA 3'.
```

Two stop codons were included in the forward primer in frame to avoid any read-through from potential earlier translation starts sites in the vector. PCR product was cloned into pTZ57R vector, and sequenced using M13FP and M13RP to confirm the clone. The PMT1 fragment was excised using BamHI and cloned into pPICZ alpha in BamHI and Bgl II sites. Clone giving 1775 bps and 576 bps fragments was selected. The PMT1 disruption cassette was transformed into *Pichia Pastoris* GS115. The plasmid was linearized using the BstEII site which is almost in the middle of PMT1 disruption fragment that is transformed into the *Pichia* strain by electroporation. The transformed clones are selected using 100 µg/ml of zeocin. A couple of hundred colonies were obtained and the individual colonies were streaked onto YPD plates. The genomic DNA was isolated from each of the clones and PCR was carried out to check the correctly disrupted clones. PMT1 knocked out was confirmed by PCR (see FIG. 2b) and also by Southern blotting (see FIG. 2c). Selected clone was deposited as MTCC5515.

Primer Sequences:

```
InSTEzRP:
                                              (SEQ ID 21)
        5' TAG CAG AGC GAG GTA TGT AGG
        CGG TGC 3'

TEFDSRP:
                                              (SEQ ID 22)
        GAG TCC GAG AAA ATC TGG AAG AGT 3'

ISCHKFP:
                                              (SEQ ID 23)
        5' GCT ACA CTA GAA GGA CAG TAT
        TTG GTA 3'

SPMT1DCFP:
                                              (SEQ ID 24)
        5' GGA CTT ATG GTT CAT CAT TGG TGA 3'
```

Example 2

Disruption of PMT6

About ~515 bps of coding sequence involving part of the PMT6 coding region was amplified using following primers

```
                                              (SEQ ID 19)
PMT6FP = 5' GGA TCC TAA TAG CTT GCC GTT AAG AGA
TAC GAT GA 3'

(SEQ ID 20)
PMT6RP = 5' GGA TCC TGA GAA TGC AAG TTT GCA CCA
GTA 3'
```

Two stop codons were included in the forward primer in frame to avoid any read-through from potential earlier translation starts sites in the vector. The PCR product was cloned into pTZ57R vector, sequenced using M13 FP and M13RP to confirm the clone.

The PMT6 disruption cassette was transformed into *Pichia Pastoris* GS115. The plasmid was linearised using the unique NdeI site which is almost in the middle of PMT6 disruption fragment that is transformed into the *Pichia* strain by electroporation. The transformed clones are selected using 100 µg/ml of zeocin. A couple of hundred colonies were obtained and the individual colonies were streaked onto YPD plates. The genomic DNA was isolated from each of the clones and PCR was carried out to screen the correctly disrupted clones (see FIG. 3b). Selected clone was deposited as MTCC5518

Example 3

Disruption of PMT4

About ~516 bps of coding sequence involving part of the PMT4 coding region was amplified using following primers.

```
                                          (SEQ ID 15)
PMT4FP = 5' GGA TCC TAA TAG GTT CAT TTC GCT ATT
CTA AGC A 3'

(SEQ ID 16)
PMT4RP = 5' GGA TCC TTT CGA CTT CAA AGG ACG GGT
T 3'
```

Two stop codons were included in the forward primer in frame to avoid any read-through from potential earlier translation starts sites in the vector. The PCR product was cloned into pTZ57R vector, sequenced using M13 FP and M13RP to confirm the clone.

The PMT4 disruption cassette was transformed into *Pichia Pastoris* GS115. The plasmid was linearised using the unique XcmI site which is almost in the middle of PMT4 disruption fragment that is transformed into the *Pichia* strain by electroporation. The transformed clones are selected using 100 µg/ml of zeocin. A couple of hundred colonies were obtained and the individual colonies were streaked onto YPD plates. The genomic DNA was isolated from each of the clones and PCR was carried out to screen the correctly disrupted clones (see FIG. 4 *b*) Selected clone was deposited as MTCC5516

Example 4

Disruption of PMT5

About ~455 bps of coding sequence involving part of the PMT5 coding region was amplified using primers

```
                                          (SEQ ID 17)
PMT5FP = 5' AGA TCT TAA TAG ATC CTA CCA GTG ATC
ATT TAC CT 3'

(SEQ ID 18)
PMT5RP = 5' AGA TCT TCA CTA ATT GGA AGG TCT AGA
ATC 3'
```

Two stop codons were included in the forward primer in frame to avoid any read-through from potential earlier translation starts sites in the vector. The PCR product was cloned into pTZ57R vector, sequenced using M13FP and M13RP to confirm the clone.

The PMT5 disruption cassette was transformed into *Pichia Pastoris* GS115. The plasmid were linearised using the unique BstEII site which is almost in the middle of PMT5 disruption fragment that is transformed into the *Pichia* strain by electroporation. The transformed clones are selected using 100 µg/ml of zeocin. A couple of hundred colonies were obtained and the individual colonies were streaked onto YPD plates. The genomic DNA was isolated from each of the clones and PCR was carried out to screen the correctly disrupted clone and the clone was confirmed by PCR. (See FIG. 5 *b*). Selected clone was deposited as MTCC5517.

Example 5

Disruption of PMT2

About ~439 bps of coding sequence involving part of the PMT2 coding region was amplified using following primer set.

```
                                          (SEQ ID 13)
PMT2FP = 5' GGA TCC TAA TAG GTG GGT TTA TTT GTC
ACA GTA 3'

(SEQ ID 14)
Pmt2RP = 5' GGA TCC GAA ACA CCC AAT CAT TGT TGG
CA 3'
```

Two stop codons were included in the forward primer in frame to avoid any read-through from potential earlier translation starts sites in the vector. The PCR product was cloned into pTZ57R vector, and sequenced using M13 FP and M13RP to confirm the clone.

The PMT2 disruption cassette was transformed into *Pichia Pastoris* GS115. The plasmid was linearised using the unique KpnI site which is almost in the middle of PMT2 disruption fragment that is transformed into *Pichia* strain by electroporation. The transformed clones are selected using 100 µg/ml of zeocin. A couple of hundred colonies were obtained and the individual colonies were streaked onto YPD plates. The genomic DNA was isolated from each of the clones and PCR was carried out to screen the correctly disrupted clones (FIG. 6).

Example 6

Reduction of Glycosylation in Insulin by PMT Knockout

*Pichia pastoris* GS115 was transformed with insulin expression construct to get clone BICC#7743 as a control for glycosylation levels; secreted insulin had glycosylation levels of 1.90-2.0 (considered 100%). PMT knockout strains MTCC 5515, MTCC 5517 and MTCC 5518 were also cloned with the insulin expression construct to compare the glycosylation levels of the secreted insulin to the control. There was a marked reduction (see FIG. 7) in the glycosylation of 61%, 31% and 28% respectively, when compared to the insulin produced by the control BICC#7743.

| CLONE NAME | STAIN NAME | GLYCOSYLATION LEVELS | % REDUCTION IN GLYCOSYLATION |
| --- | --- | --- | --- |
| BICC #7743 | GS115 | 1.90-2.20 | 0 |
| BICC #9104 | MTCC5515 | 0.86 | 61 |
| BICC #9106 | MTCC5517 | 1.5 | 31 |
| BICC #9107 | MTCC5518 | 1.59 | 28 |

Example 7

Reduction of Glycosylation in Insulin Analog 1 by PMT Knockout

*Pichia pastoris* GS115 was transformed with insulin expression construct to get clone BICC#7744 as a control for glycosylation levels; secreted insulin had glycosylation levels of 1.66 (considered 100%). PMT knockout strains MTCC 5515 was also cloned with the insulin expression construct to compare the glycosylation levels of the secreted insulin to the control. There was a marked reduction (FIG. 8) in the glycosylation of 46% when compared to the insulin analog 1, produced by the control BICC#7744.

| CLONE NAME | STAIN NAME | GLYCOSYLATION LEVELS | % REDUCTION IN GLYCOSYLATION |
|---|---|---|---|
| BICC #7744 | Parent | 1.66 | 0 |
| BICC #9118 | MTCC5515 | 0.9 | 46 |

Example 8

Reduction of Glycosylation in Insulin Analog 2 by PMT Knockout

*Pichia pastoris* GS115 was transformed with insulin expression construct to get clone BICC#7996 as a control for glycosylation levels; secreted insulin had glycosylation levels of 1.92 (considered 100%). PMT knockout strains MTCC 5515 was also cloned with the insulin expression construct to compare the glycosylation levels of the secreted insulin to the control. There was a marked reduction (FIG. 9) in the glycosylation of 65% when compared to the insulin analog 1, produced by the control BICC#7996.

| CLONE NAME | STAIN NAME | GLYCOSYLATION LEVELS | % REDUCTION IN GLYCOSYLATION |
|---|---|---|---|
| BICC #7996 | Parent | 1.92 | 0 |
| BICC #9125 | MTCC5515 | 0.67 | 65 |

We claim:

1. A method of reducing glycosylation of insulin precursor or its analogs, wherein its analogs retain a biological property of insulin, represented by formula I

X-B-Y-A wherein,

X is a leader peptide sequence comprising at least one amino acid,

B is the amino acid sequence of the B chain of the insulin molecule or analogs,

Y is a linker peptide comprising at least one amino acid,

A is the amino acid sequence of the A chain of the insulin molecule or analogs, and the A and B chain can be modified by amino acid substitution, deletion and/or additions; produced from a methylotrophic yeast enabled through inactivation of at least one of the genes selected from the group comprising PMT1 and PMT5 having a nucleotide sequence represented by SEQ ID Nos. 1 and 4 respectively, said sequences encode for the protein mannosyl transferase or a functional part thereof.

2. The method according to claim 1, wherein said methylotrophic yeast belongs to *Pichia* sp.

3. The method according to claim 2, wherein said methylotrophic yeast is *Pichia pastoris*.

4. The method according to claim 1, wherein the glycosylation is O-glycosylation.

5. The method according to claim 1, wherein the glycosylation is reduced by at least 10% to about 99%.

6. The method according to claim 5, wherein the glycosylation is reduced by 25%.

7. The method according to claim 5, wherein the glycosylation is reduced by 65%.

8. A vector containing the protein mannosyl transferase gene or a functional part thereof selected from the group consisting of PMT1 and PMT5 genes having a nucleotide sequence represented by SEQ ID Nos. 1 and 4 respectively.

9. The vector according to claim 8, wherein said vector is transformed into the methylotrophic yeast for reducing or modifying glycosylation of the protein.

10. The vector according to claim 8, wherein said methylotrophic yeast belongs to *Pichia* sp.

11. The vector according to claim 10, wherein said methylotrophic yeast is *Pichia pastoris*.

12. A process for production of knock-out strain of methylotrophic yeast, said process comprising:
   (a) a vector incorporating a nucleic acid sequence capable of homologous recombination containing a target nucleic acid sequence encoding at least one of the genes selected from the group consisting of PMT1 and PMT5 having a nucleotide sequence represented by SEQ ID Nos. 1 and 4 respectively and a nucleic acid sequence coding for a selection marker;
   (b) culturing cells under conditions to permit homologous recombination between the DNA encoding the target gene in the vector and in the host cell to occur thereby leading to disruption of the target gene in the host cell;
   (c) selecting host cells with the inactivated target gene, for production of the knock-out strain of methylotrophic yeast.

13. A knock-out strain of a methylotrophic yeast, said strain having at least one inactivated gene selected from the group consisting of PMT1 and PMT5 having a nucleotide sequence represented by SEQ ID Nos. 1 and 4 respectively.

14. PMT1 genes inactivated strain as in claim 13, Accession number is MTCC5515.

15. PMT5 genes inactivated strain as in claim 13, Accession number is MTCC5517.

16. The knock-out strain according to claim 13, wherein said host strain yields protein with reduced level of glycosylation compared to protein product expressed in an unaltered host strain.

17. The knock-out strain according to claim 13, wherein said strain expresses a protein, wherein glycosylation is reduced by at least 25%.

18. The knock-out strain according to claim 13, wherein said strain expresses a protein wherein, glycosylation is reduced by at least 65%.

* * * * *

UNITED STATES PATENT AND TRADEMARK OFFICE
CERTIFICATE OF CORRECTION

PATENT NO.           : 8,778,659 B2                                              Page 1 of 1
APPLICATION NO.      : 13/578403
DATED                : July 15, 2014
INVENTOR(S)          : Govindappa et al.

It is certified that error appears in the above-identified patent and that said Letters Patent is hereby corrected as shown below:

IN THE CLAIMS

In column 35, line 59, in Claim 1, after "analogs," insert --wherein the insulin analogs retain a biological activity of insulin,--, therefor In column 35, line 61, in Claim 1, delete "produced" and insert --said method comprising producing said insulin precursor or insulin analogs represented by formula I--, therefor In column 35, line 62, in Claim 1, delete "inactivation of" and insert --inactivating--, therefor In column 35, line 63-64, in Claim 1, delete "comprising" and insert --consisting of--, therefor In column 35, line 66, in Claim 1, delete "encode" and insert --encoding--, therefor Signed and Sealed this
Fourth Day of November, 2014

Michelle K. Lee
*Deputy Director of the United States Patent and Trademark Office*